(12) United States Patent
Picot

(10) Patent No.: US 12,268,586 B2
(45) Date of Patent: Apr. 8, 2025

(54) ELASTIC LAMINATE WITH HOOKS

(71) Applicant: APLIX, Le Cellier (FR)

(72) Inventor: Lionel Picot, Le Cellier (FR)

(73) Assignee: Aplix, Le Cellier (FR)

( * ) Notice: Subject to any disclaimer, the term of this patent is extended or adjusted under 35 U.S.C. 154(b) by 748 days.

(21) Appl. No.: 17/615,187

(22) PCT Filed: Jul. 2, 2020

(86) PCT No.: PCT/EP2020/068706
§ 371 (c)(1),
(2) Date: Nov. 30, 2021

(87) PCT Pub. No.: WO2021/001492
PCT Pub. Date: Jan. 7, 2021

(65) Prior Publication Data
US 2022/0233366 A1    Jul. 28, 2022

(30) Foreign Application Priority Data

Jul. 4, 2019   (FR) ...................................... 19 07472

(51) Int. Cl.
*A61F 13/58* (2006.01)
*A61F 13/56* (2006.01)
(Continued)

(52) U.S. Cl.
CPC ........ *A61F 13/625* (2013.01); *A61F 13/5638* (2013.01); *A61F 2013/15861* (2013.01); *Y10T 428/24017* (2015.01)

(58) Field of Classification Search
None
See application file for complete search history.

(56) References Cited

U.S. PATENT DOCUMENTS

| 2009/0008023 A1 | 1/2009 | Verhaert et al. |
| 2012/0022490 A1 | 1/2012 | Marche et al. |
| 2019/0248104 A1 | 8/2019 | Moinard et al. |

FOREIGN PATENT DOCUMENTS

| WO | 2010109087 A1 | 9/2010 |
| WO | 2018011516 A1 | 1/2018 |

OTHER PUBLICATIONS

International Search Report mailed Jul. 30, 2020 in related application No. PCT/EP2020/068706.

*Primary Examiner* — Alexander S Thomas
(74) *Attorney, Agent, or Firm* — Renner, Kenner, Greive, Bobak, Taylor & Weber

(57) ABSTRACT

Elastic laminate with hooks comprising an upper layer (2) of nonwoven fabric extending in width in a direction CD and in length in a direction MD, a web (5) with hooks (10) comprising a strip, in particular made of thermoplastic material, from which hooks protrude, and which is attached onto the upper face of the upper layer of nonwoven fabric, the hooks being intended to engage with loops according to a hook-and-loop fastening system, an elastic film (3; 4) extending in the direction CD over a width less than or equal to the width of the upper layer (2) of nonwoven fabric, the upper face of the elastic film (3; 4) being attached to the lower side of the upper layer of nonwoven fabric, the web with hooks extending between respective side end points, left-hand and right-hand respectively, and characterised in that one (Pg6; Pd6) of the two side end points (Pg6, Pd6), left-hand and right-hand respectively, of the web (5) with hooks is located vertically in line with a point of the elastic film.

22 Claims, 26 Drawing Sheets

(51) Int. Cl.
*A61F 13/62* (2006.01)
*A61F 13/15* (2006.01)

[Fig. 1A]
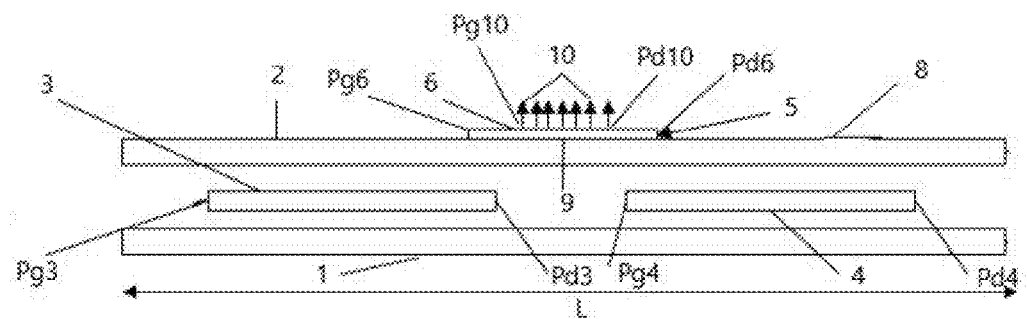
[Fig. 1B]
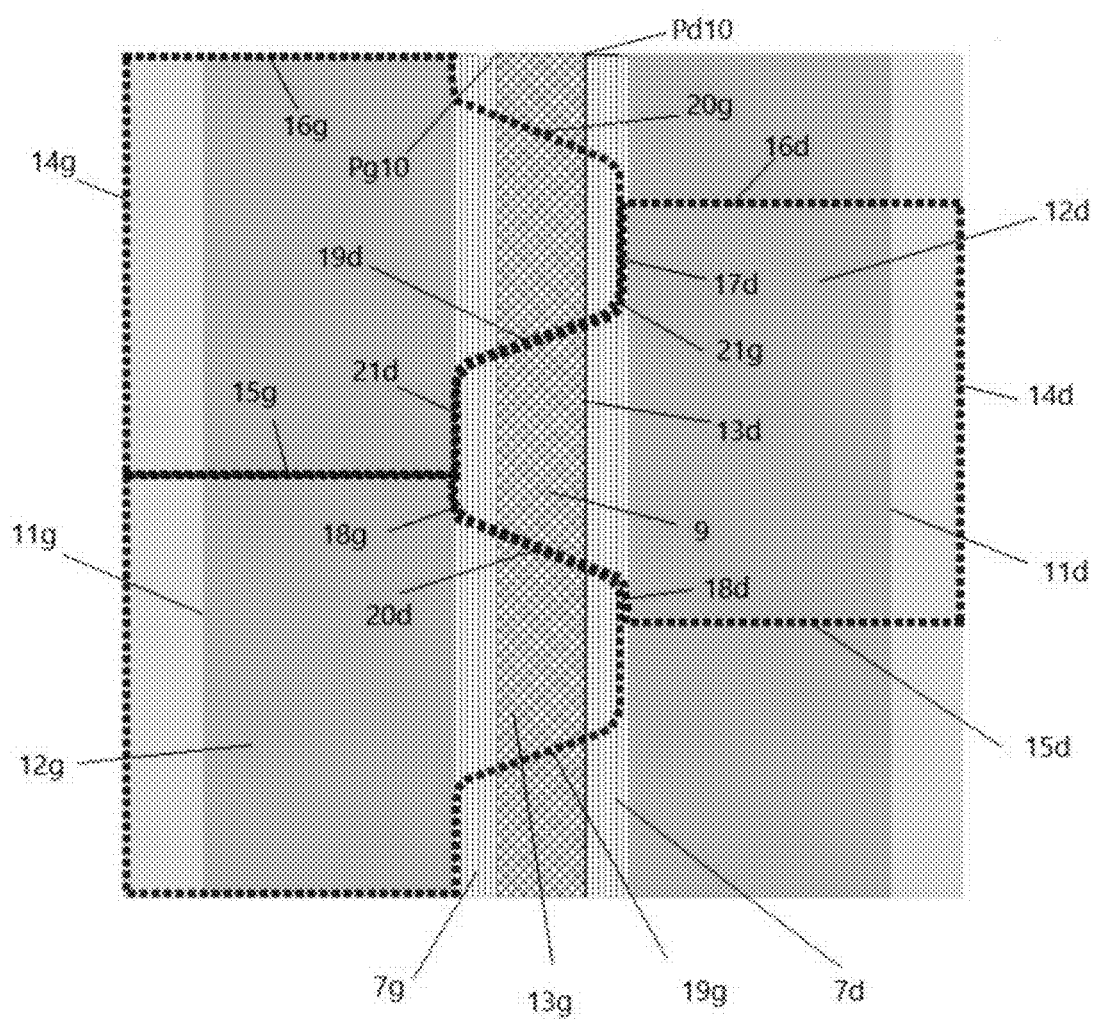

[Fig. 2]
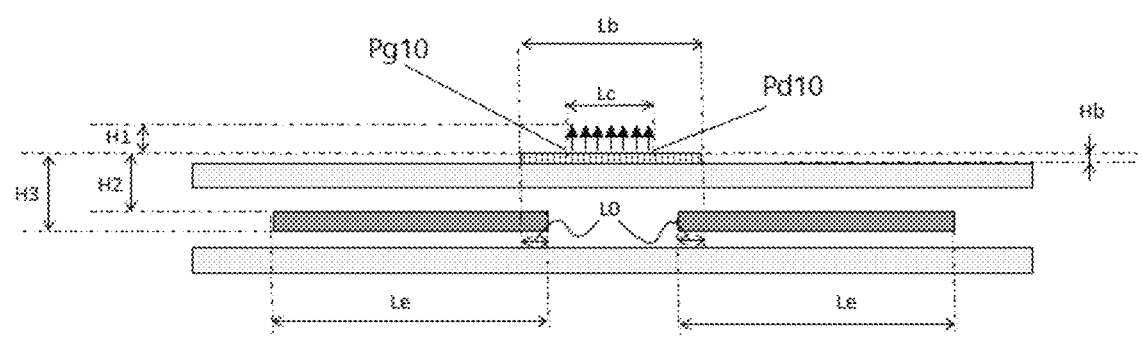
[Fig. 3A]
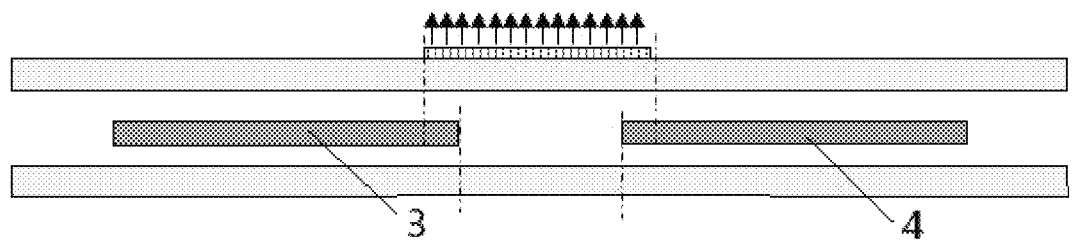

[Fig. 3B]
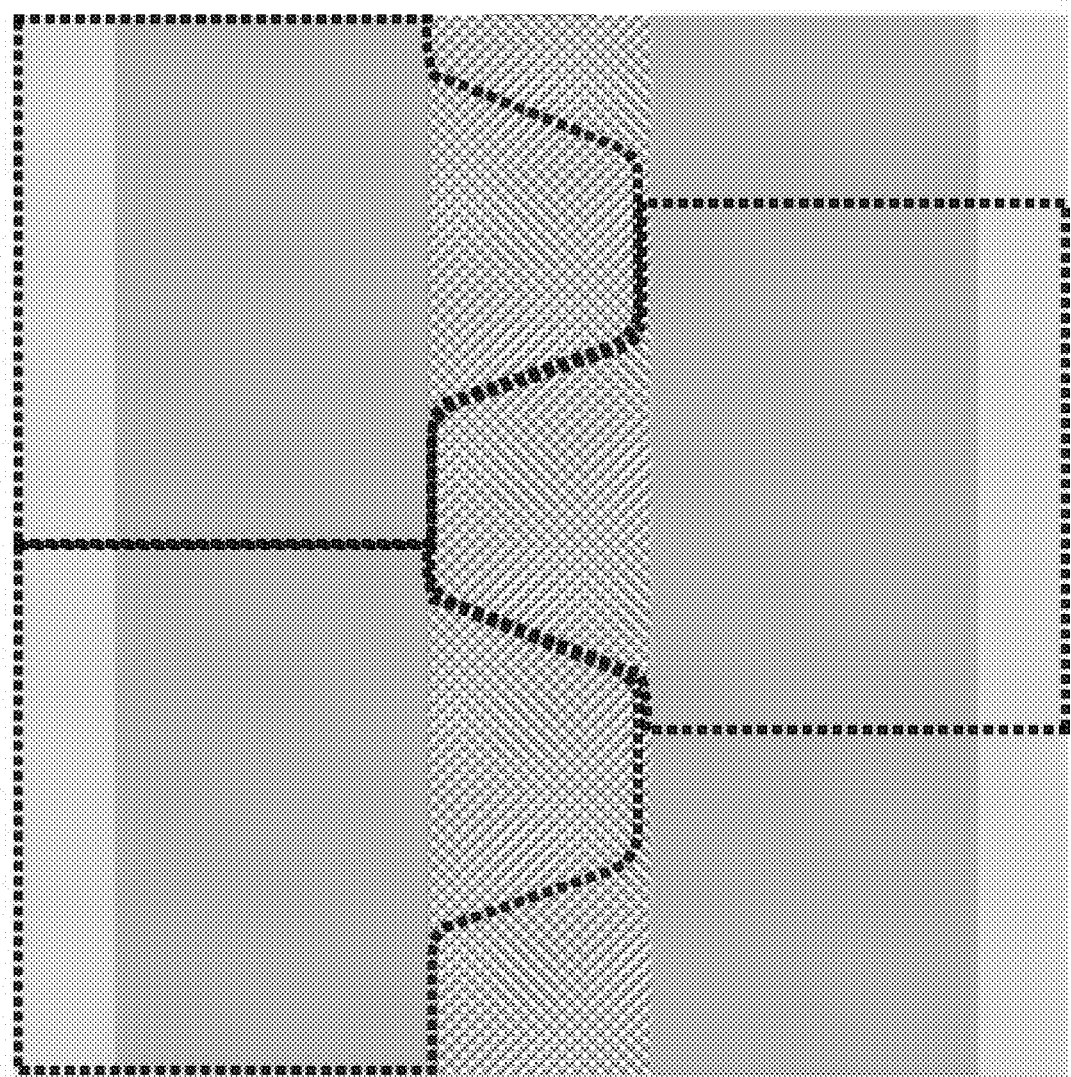
[Fig. 4A]
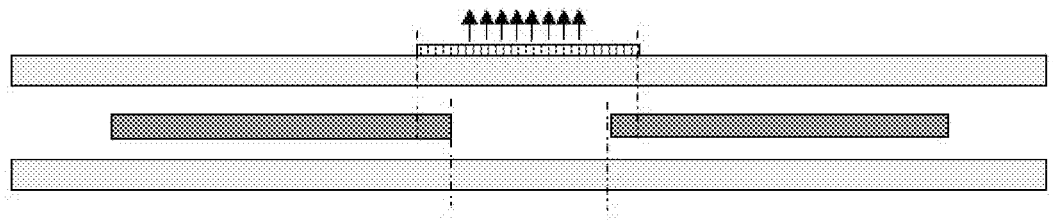

[Fig. 4B]
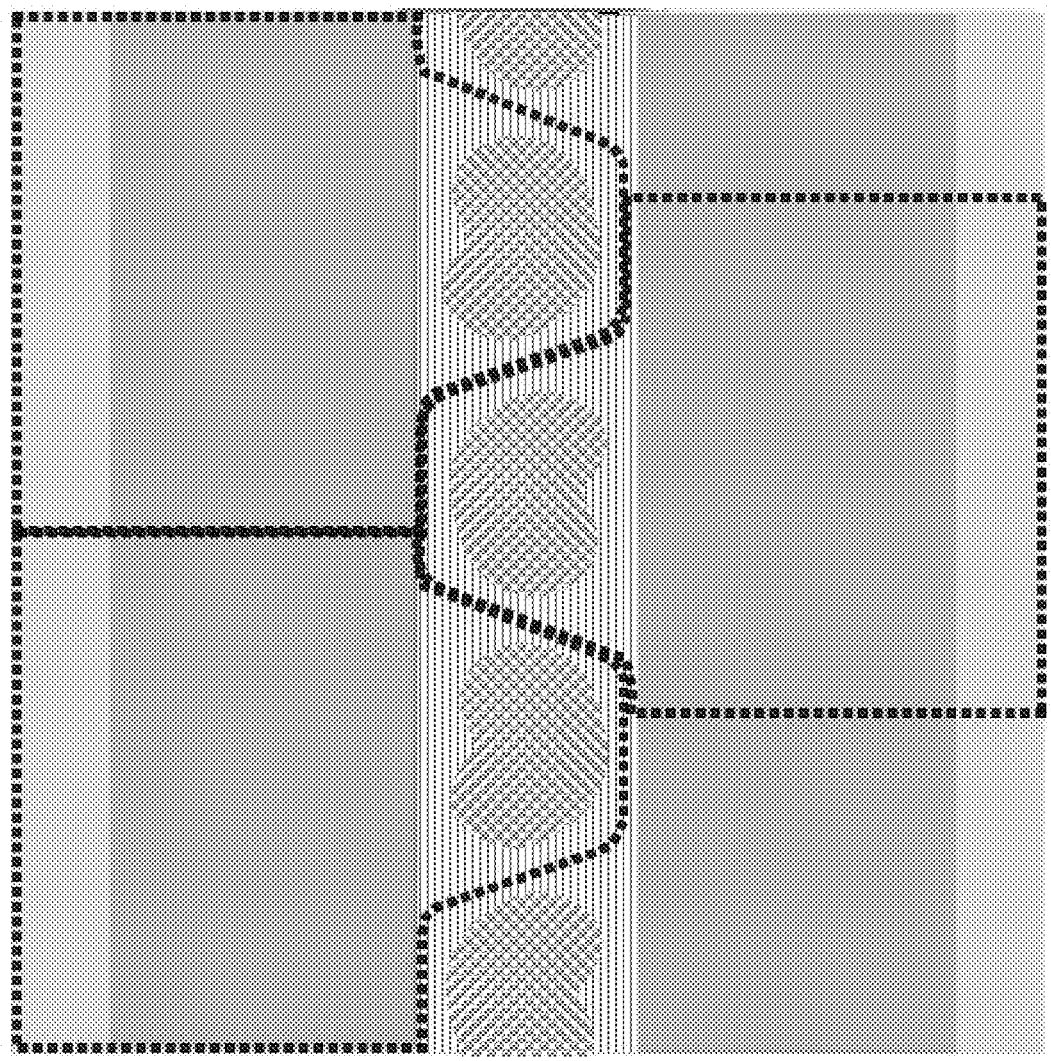
[Fig. 5A]
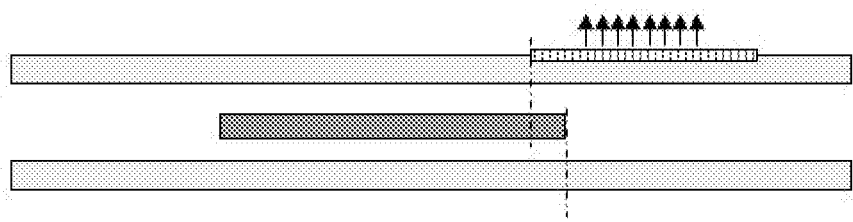

[Fig. 5B]
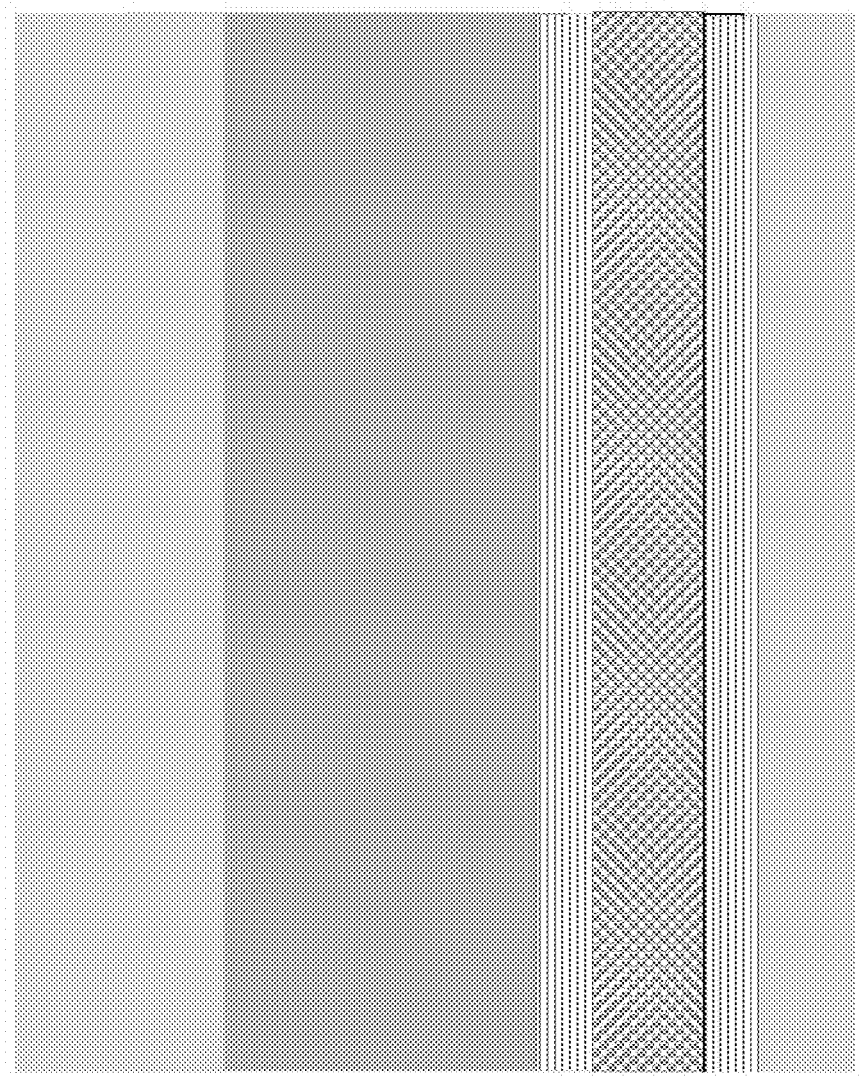
[Fig. 6A]
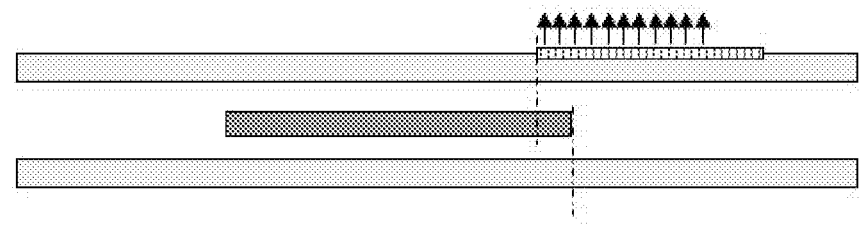

[Fig. 6B]
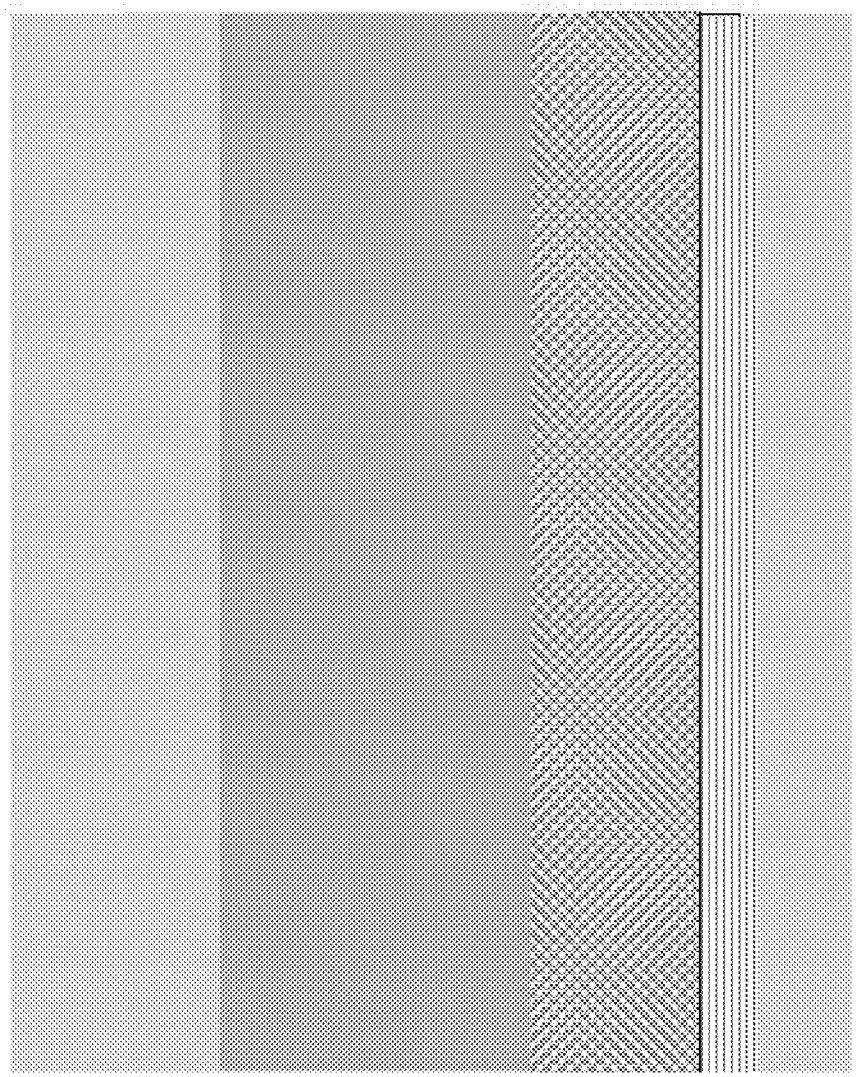
[Fig. 7A]
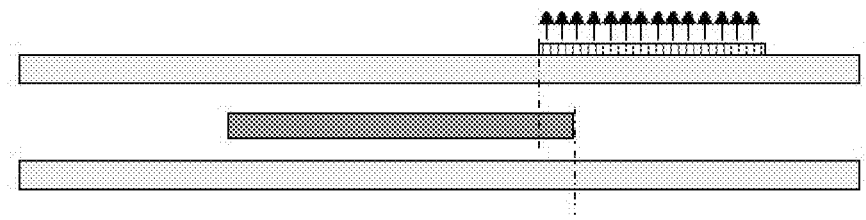

[Fig. 7B]
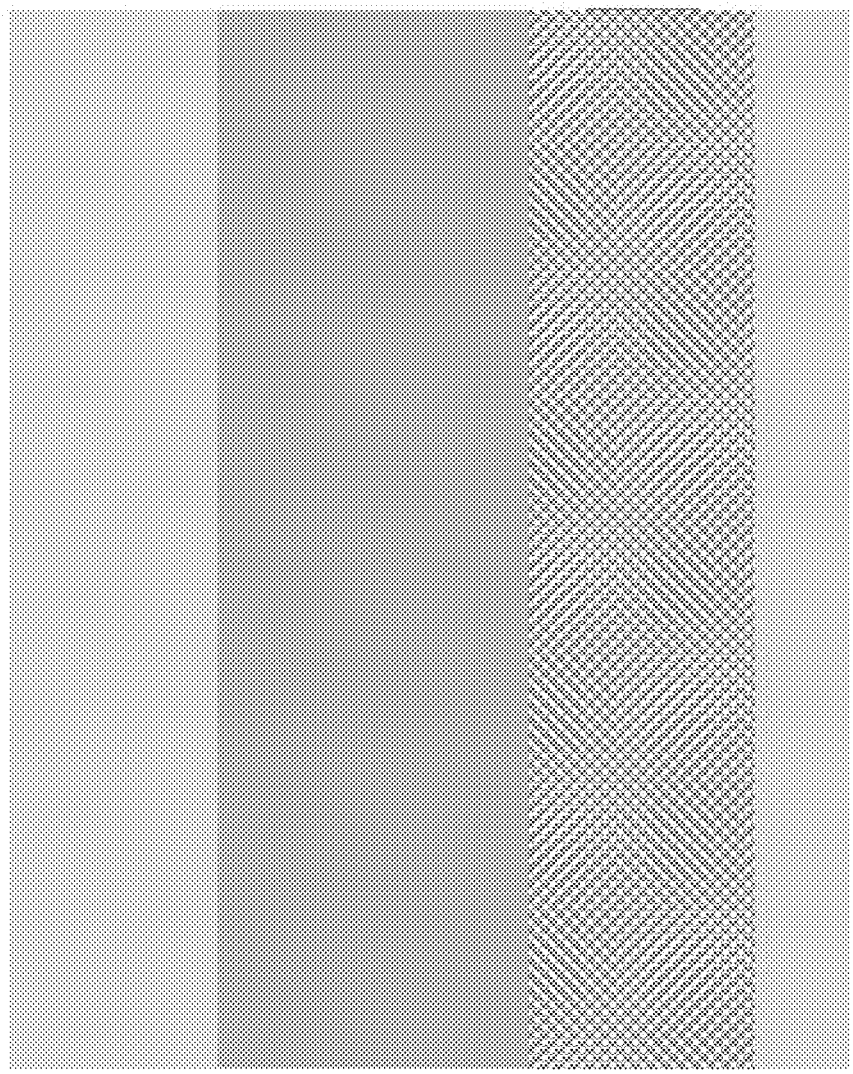
[Fig. 8A]
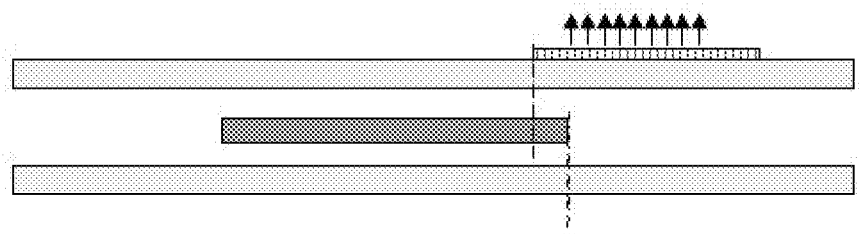

[Fig. 8B]
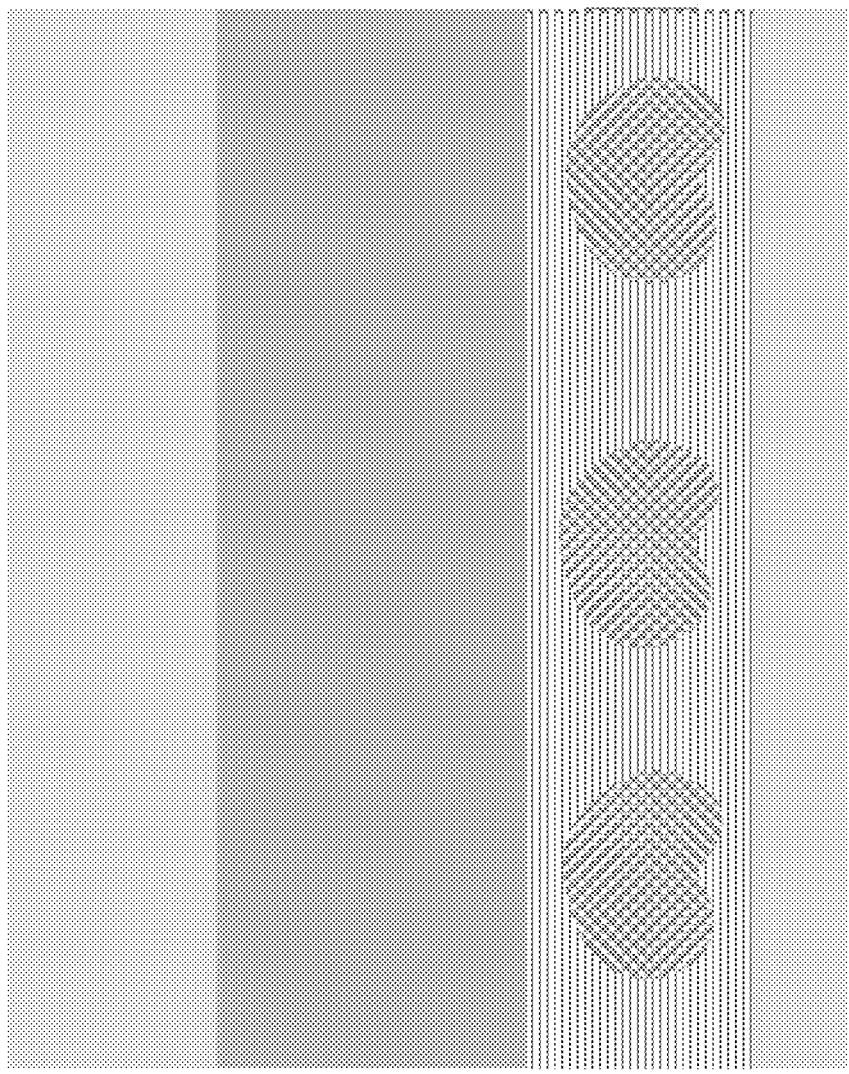
[Fig. 9A]
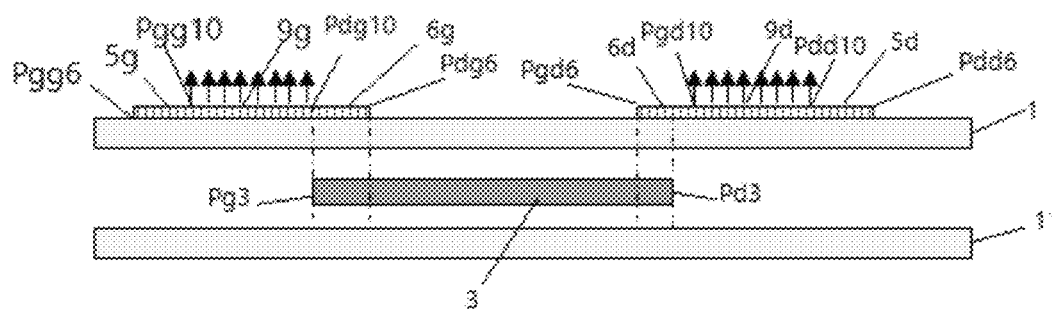

[Fig. 9B]
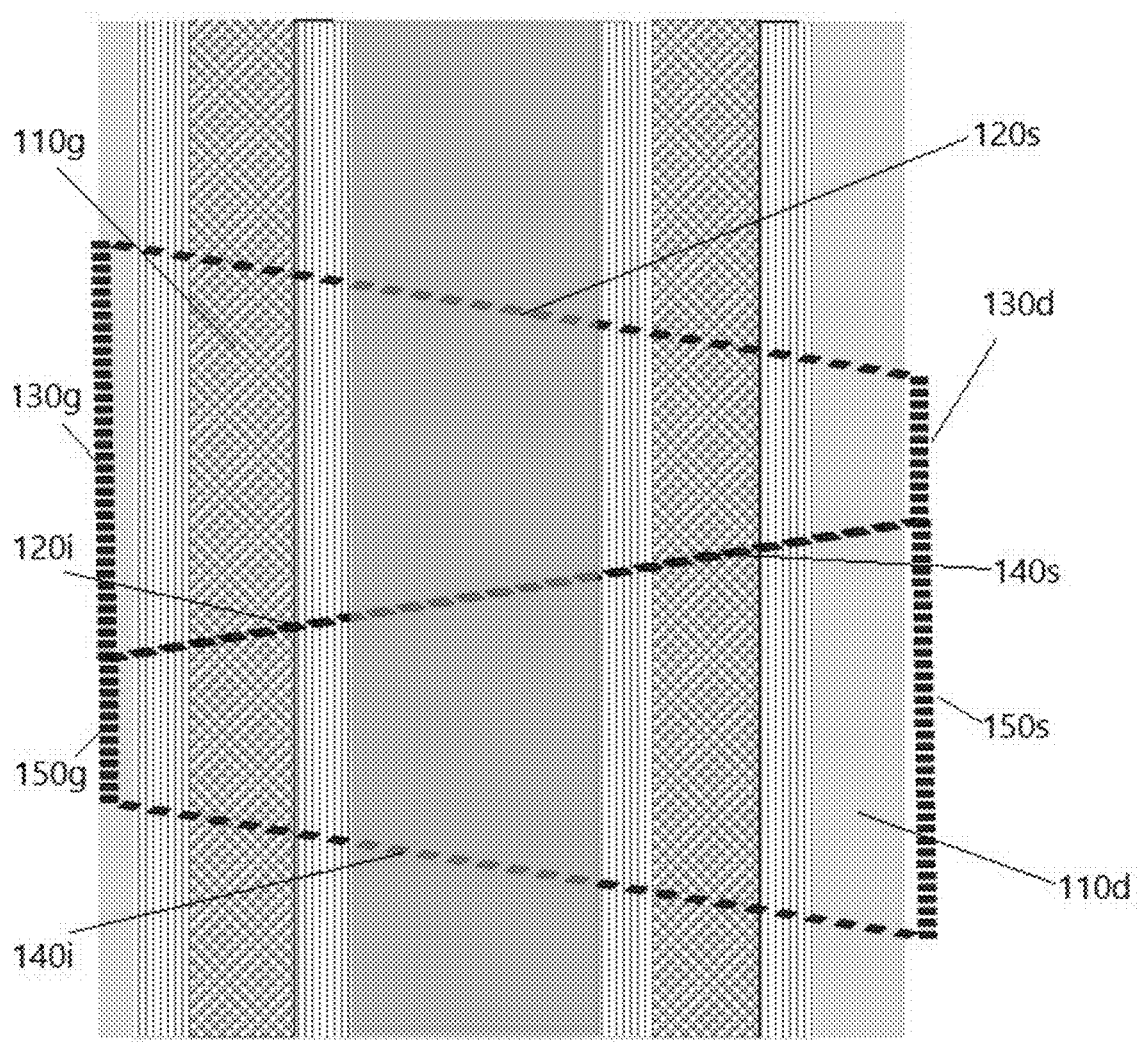
[Fig. 10A]
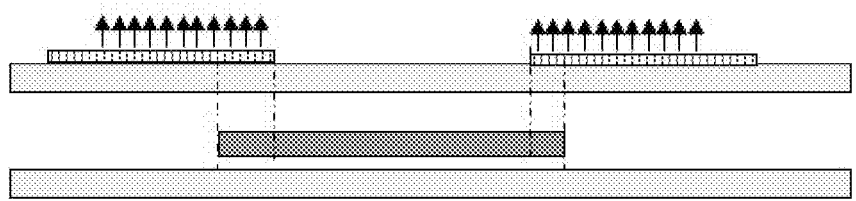

[Fig. 10B]
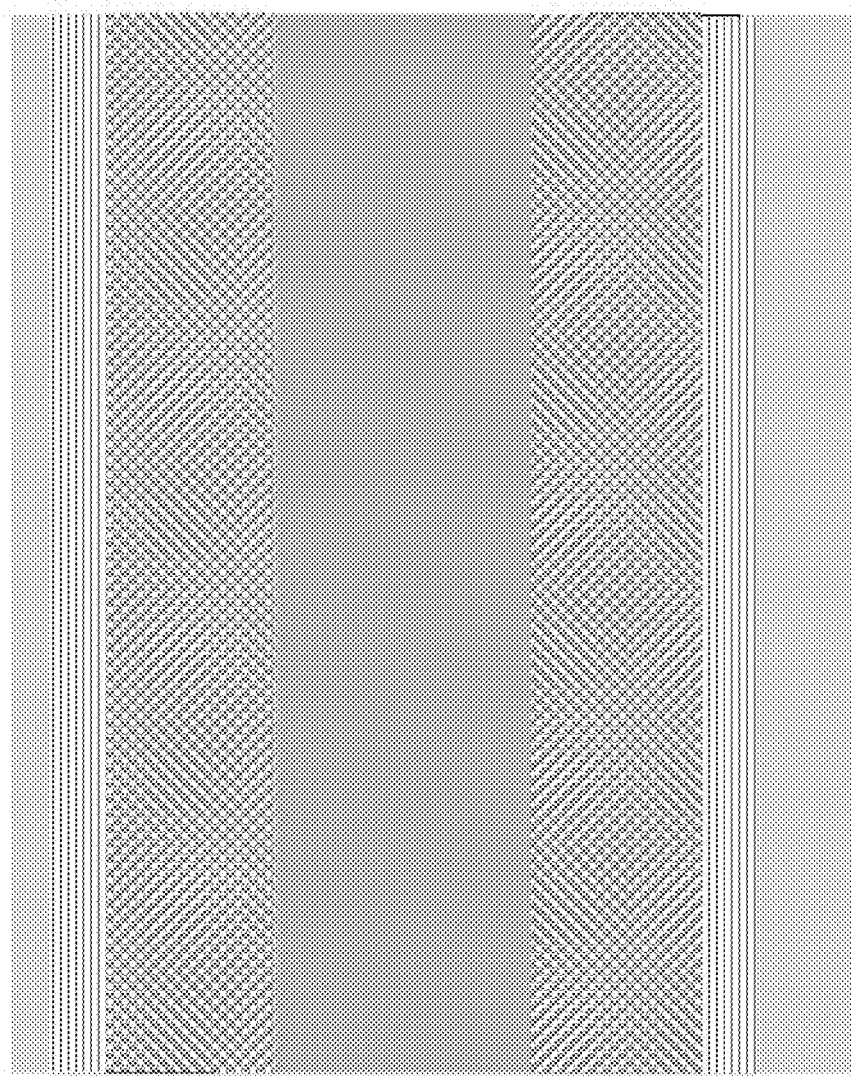
[Fig. 11A]
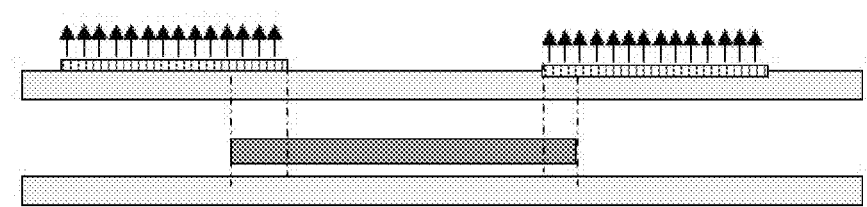

[Fig. 11B]
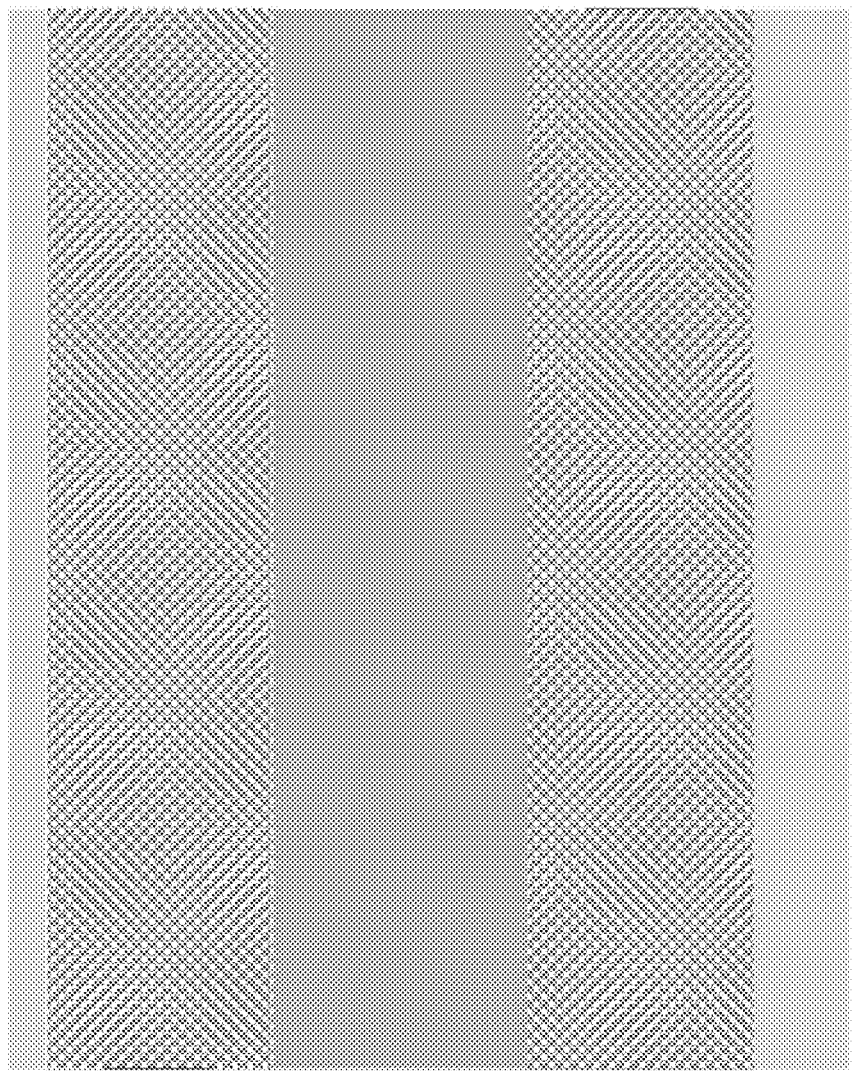
[Fig. 12A]
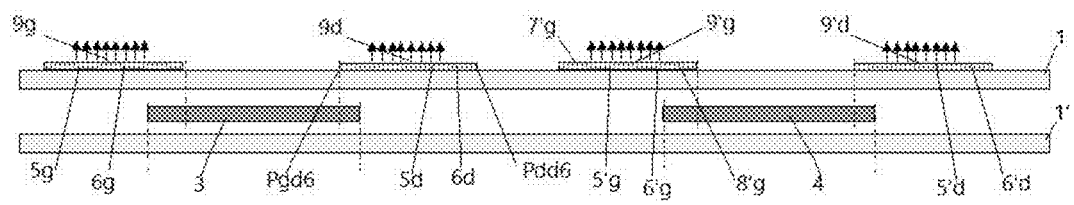

[Fig. 12B]
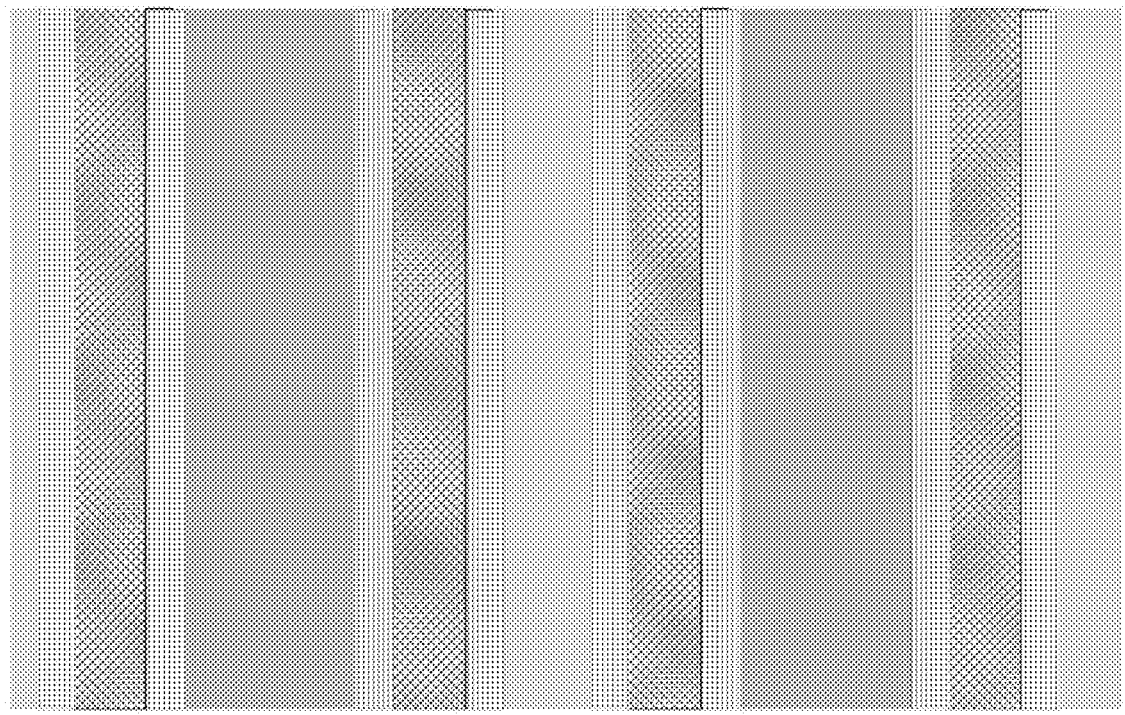
[Fig. 13A]
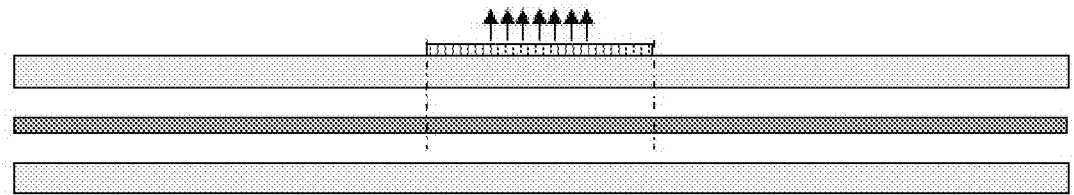

[Fig. 13B]
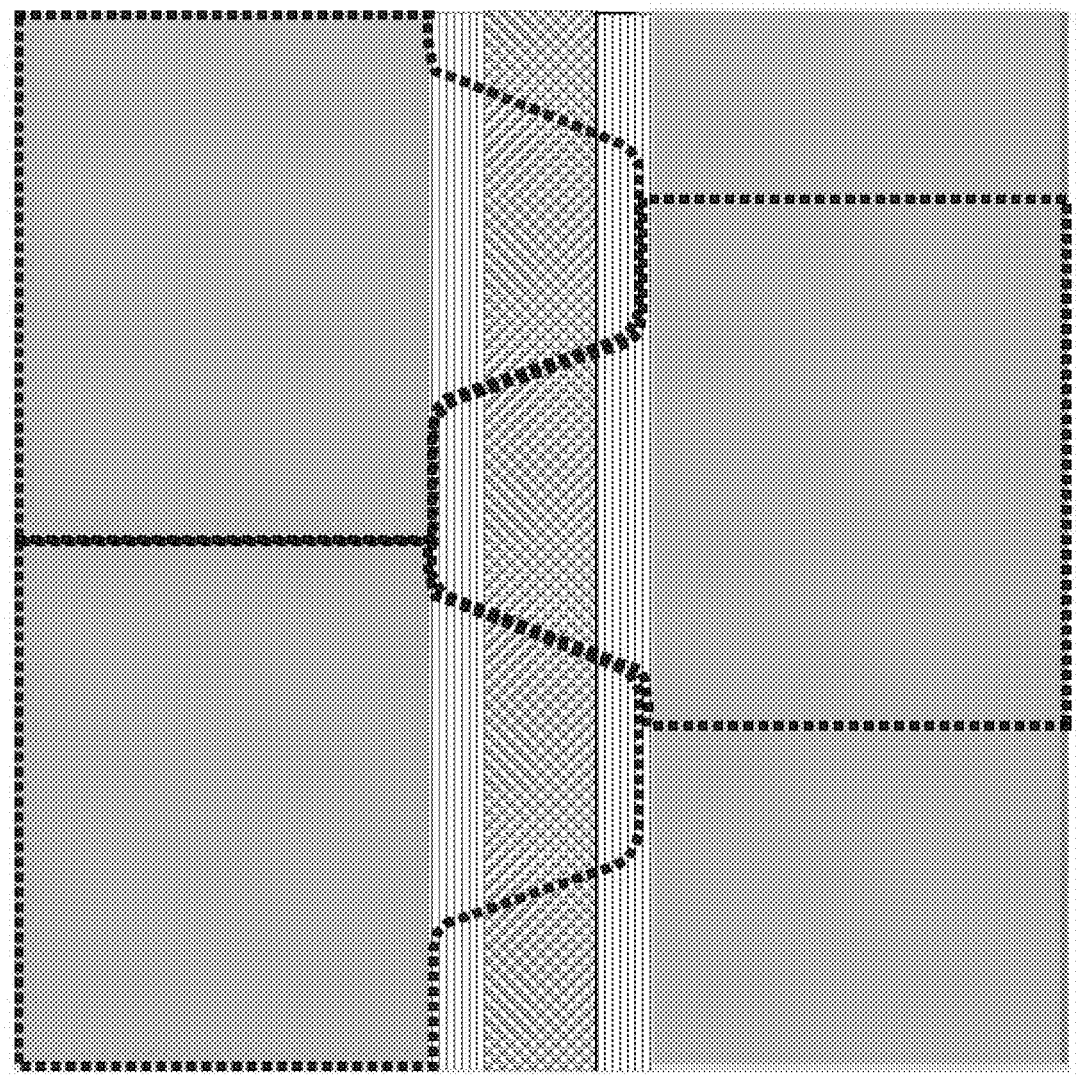
[Fig. 14A]
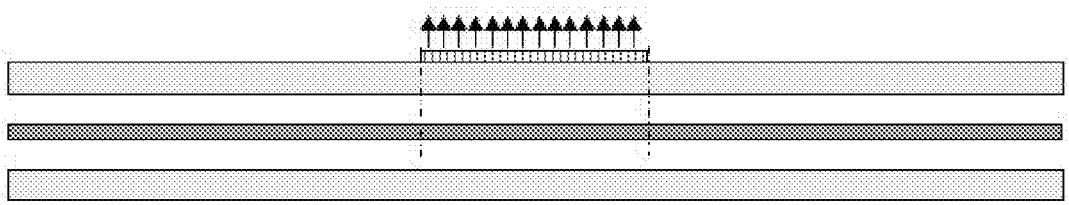

[Fig. 14B]
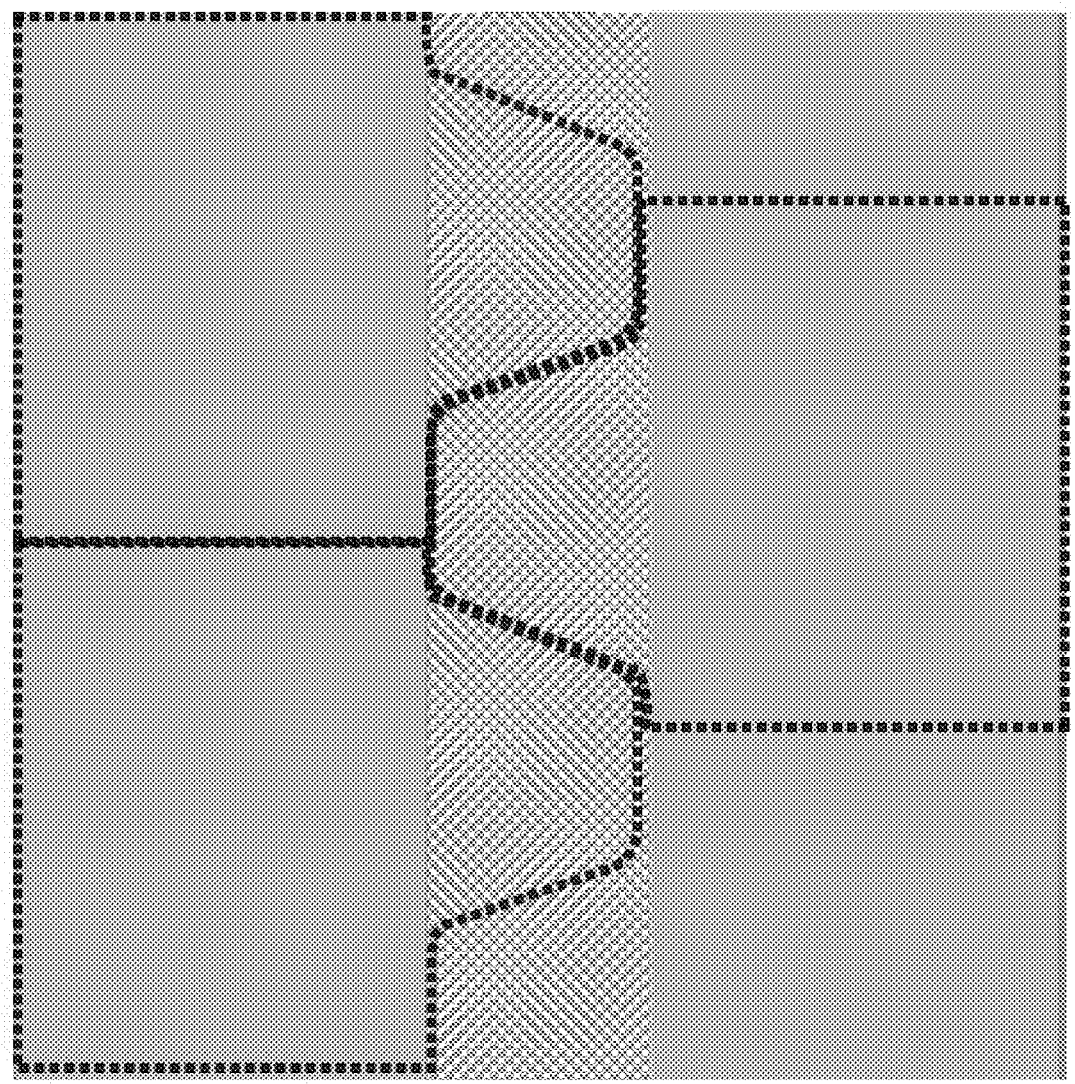
[Fig. 15A]
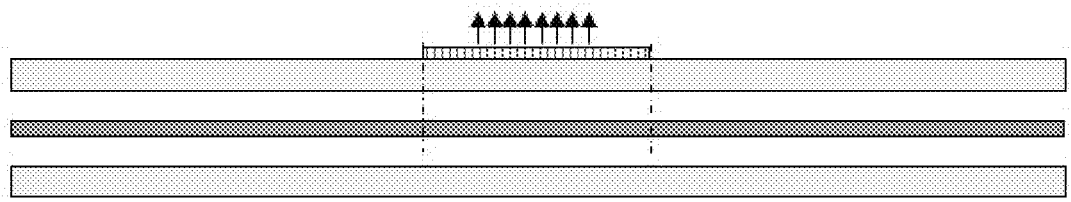

[Fig. 15B]
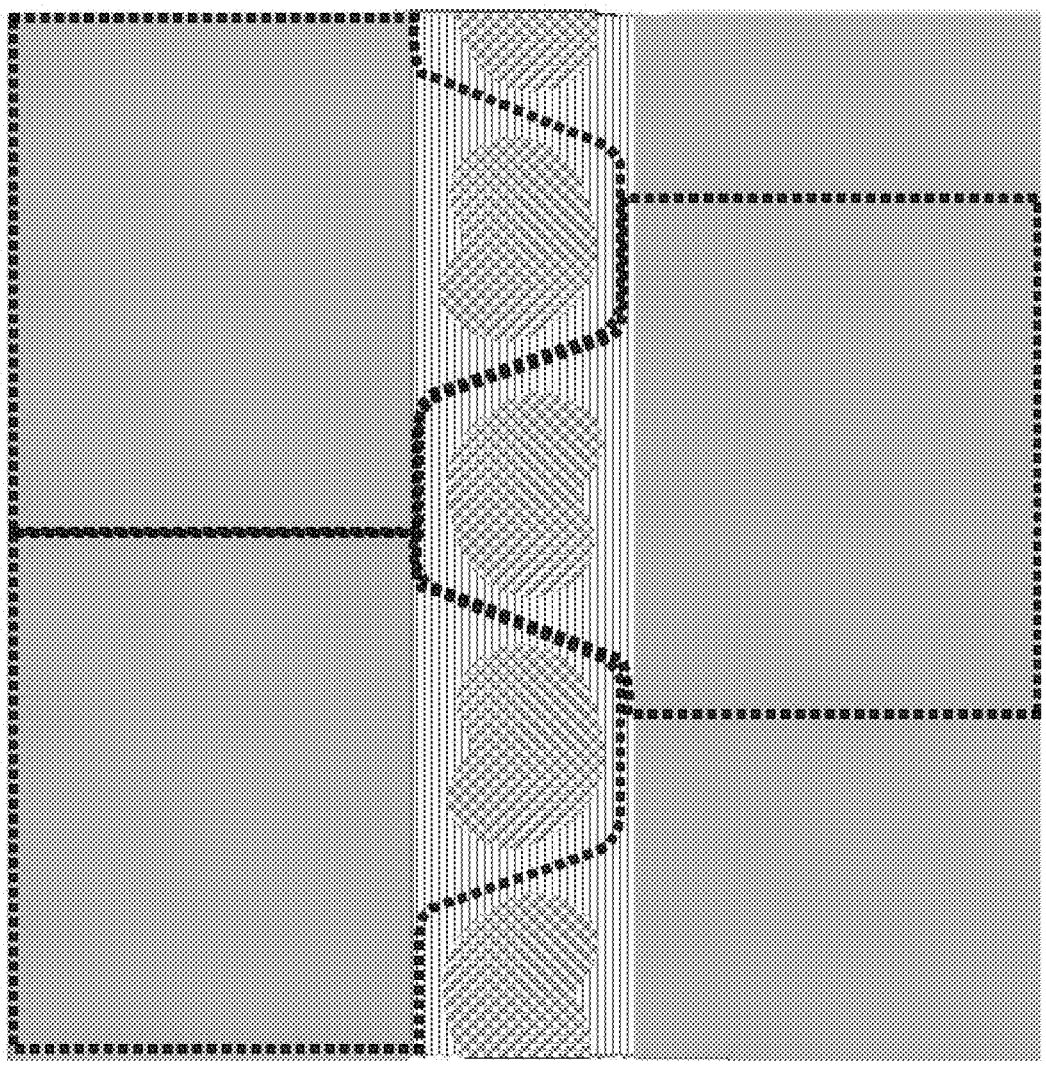
[Fig. 16A]
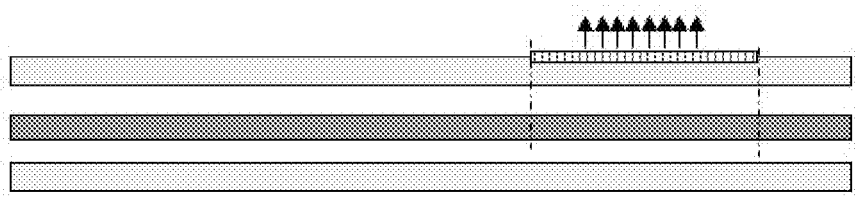

[Fig. 16B]
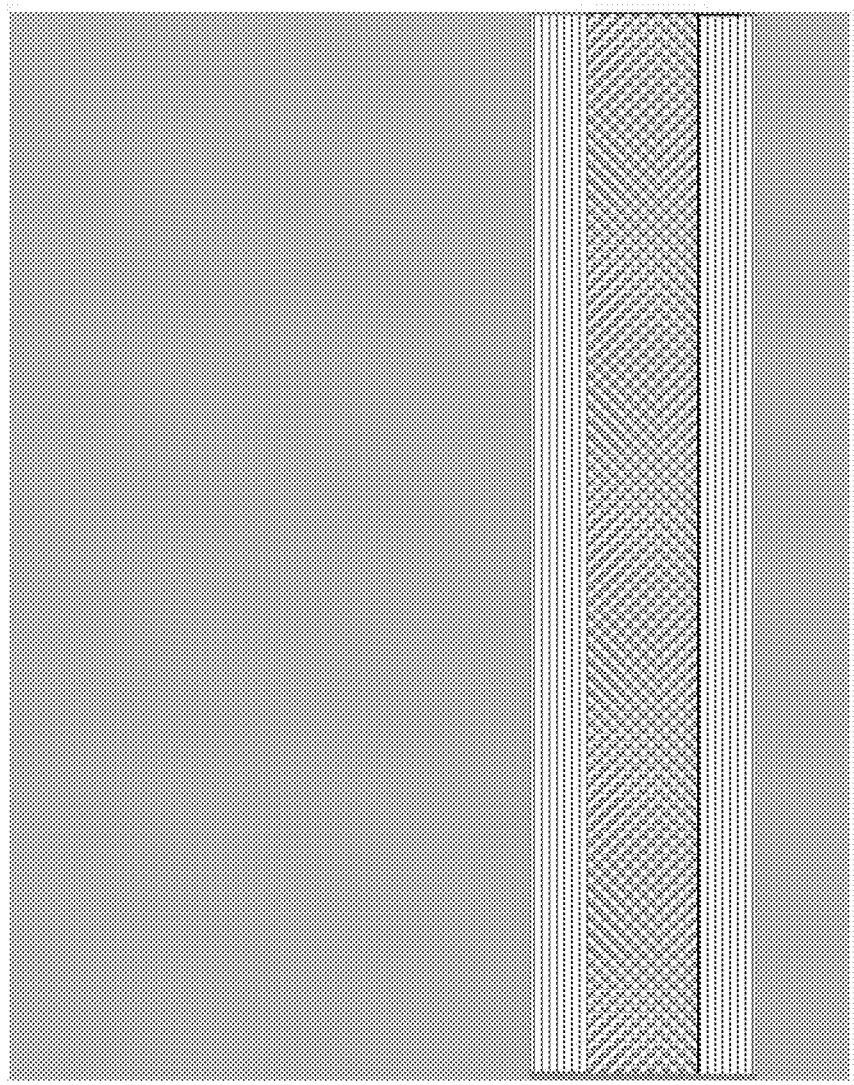
[Fig. 17A]
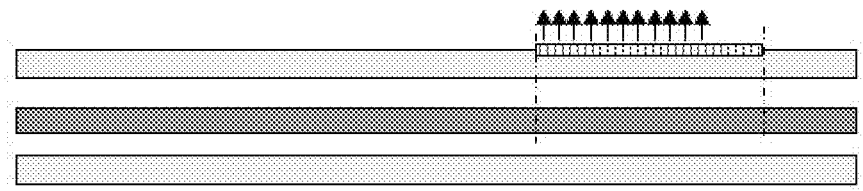

[Fig. 17B]
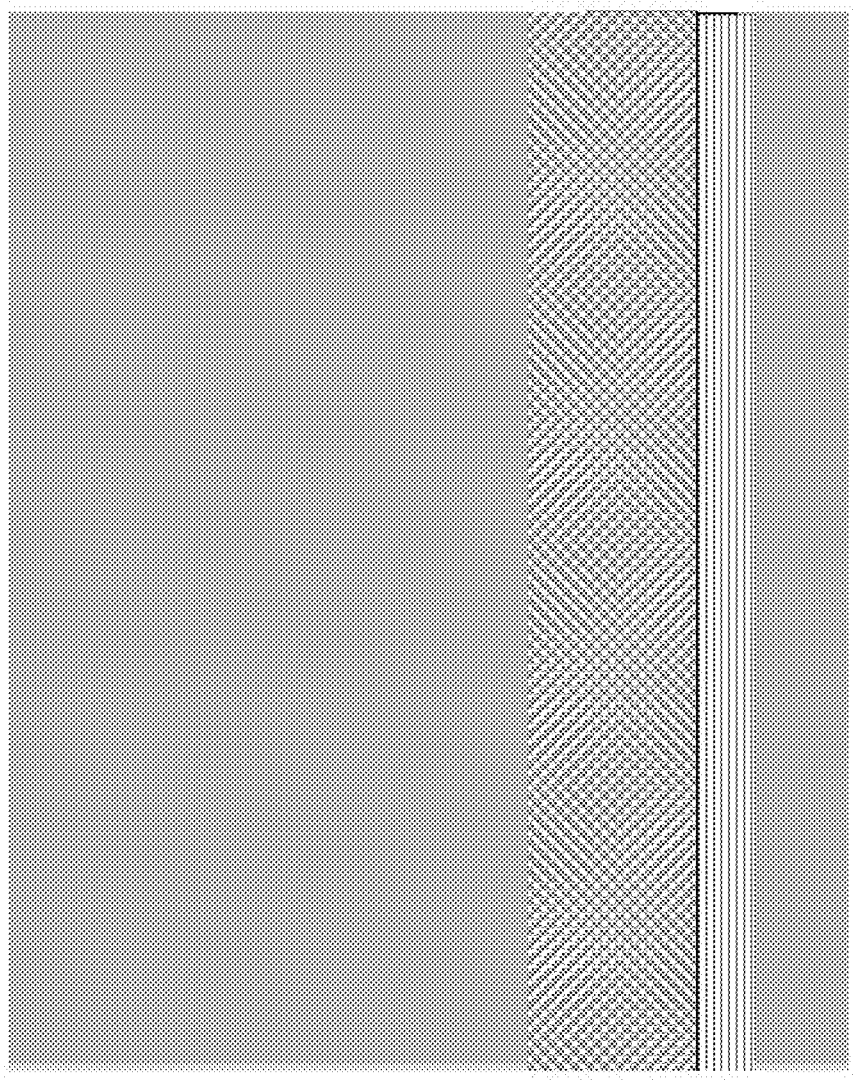
[Fig. 18A]
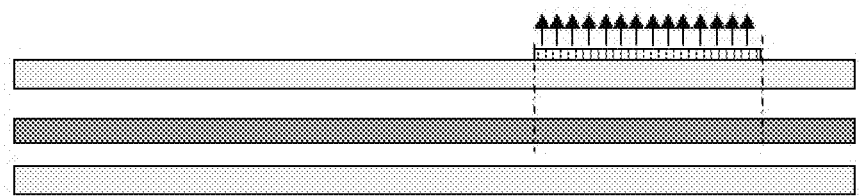

[Fig. 18B]
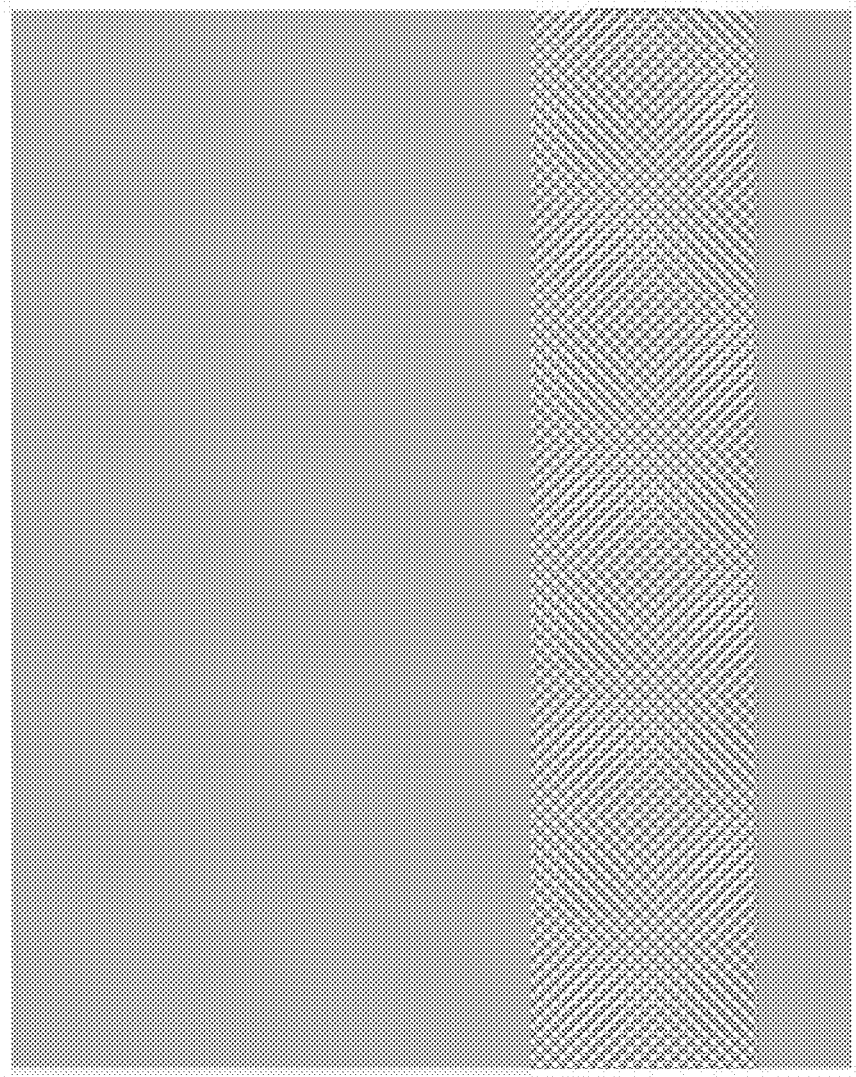
[Fig. 19A]
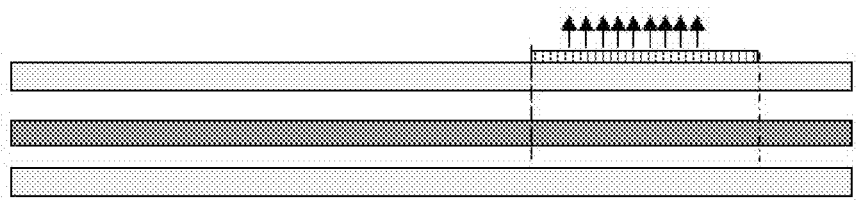

[Fig. 19B]
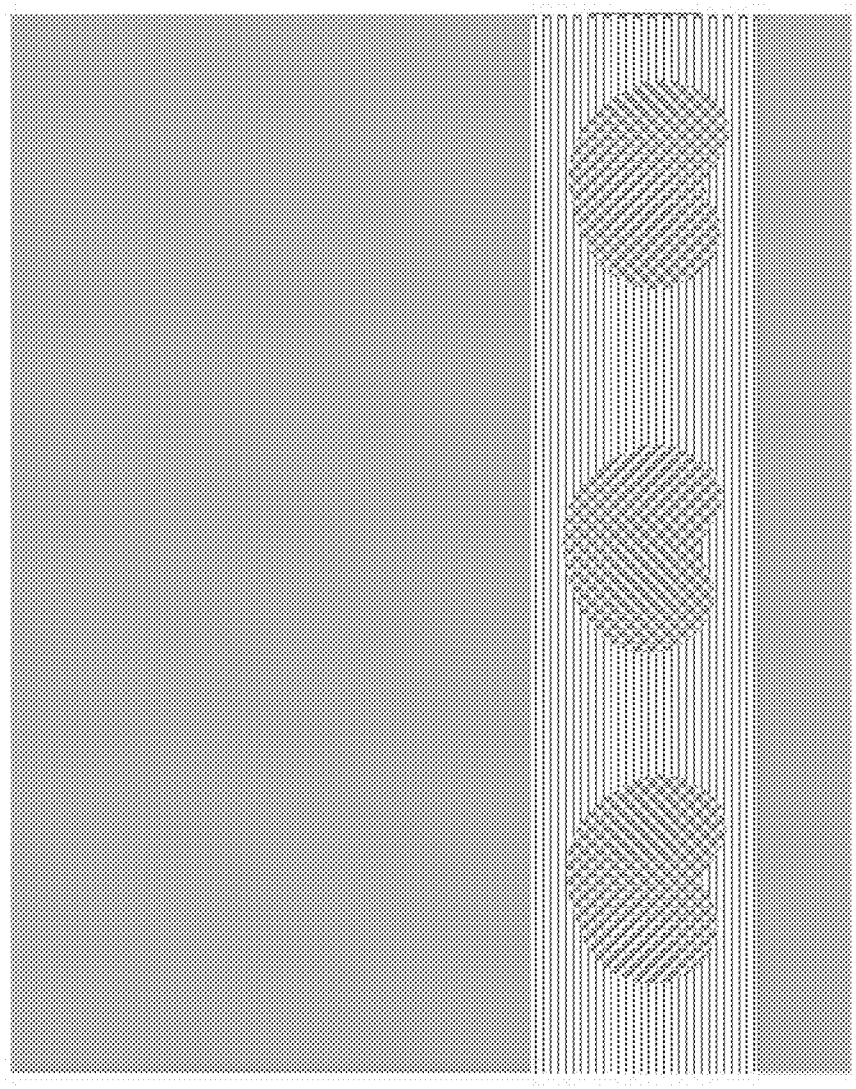
[Fig. 20A]
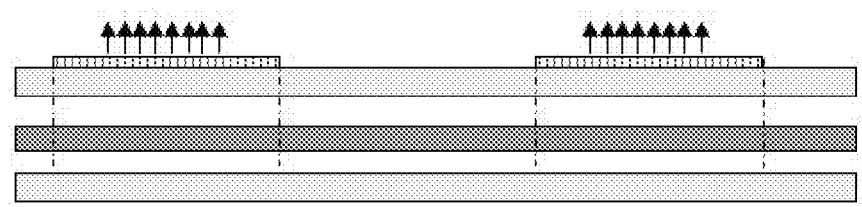

[Fig. 20B]
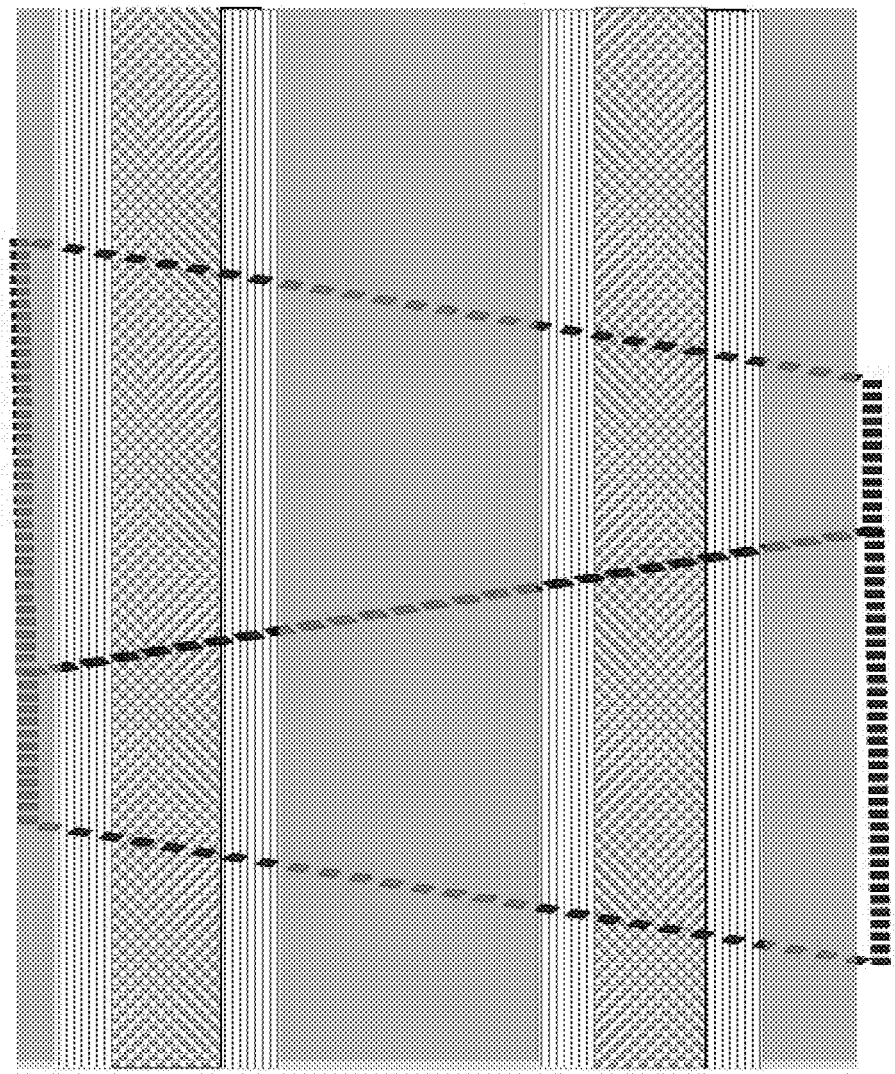
[Fig. 21A]
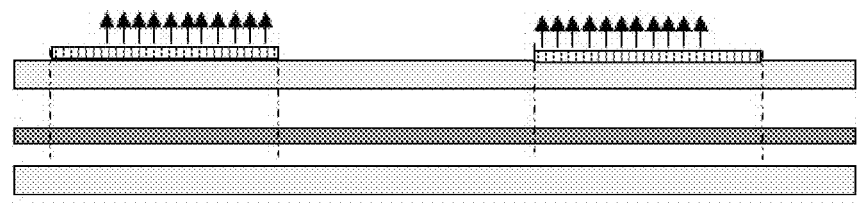

[Fig. 21B]
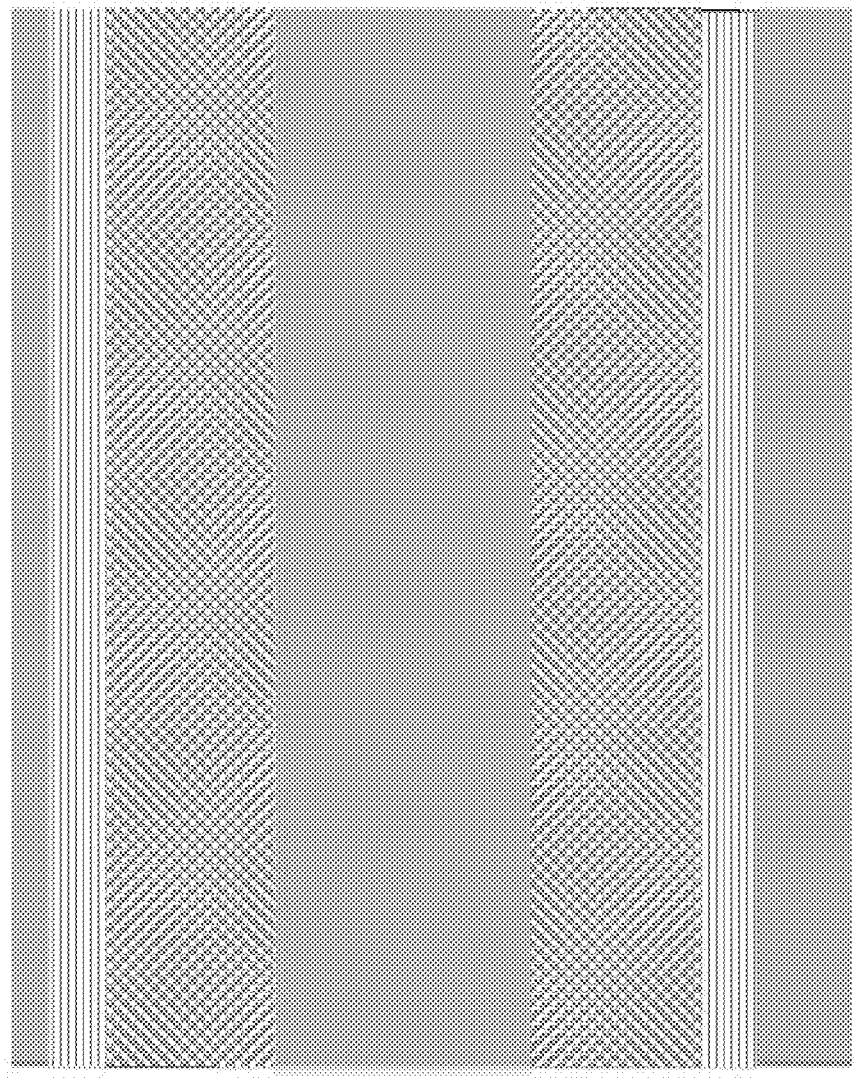
[Fig. 22A]
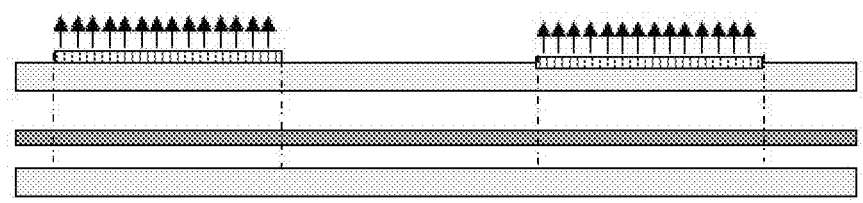

[Fig. 22B]
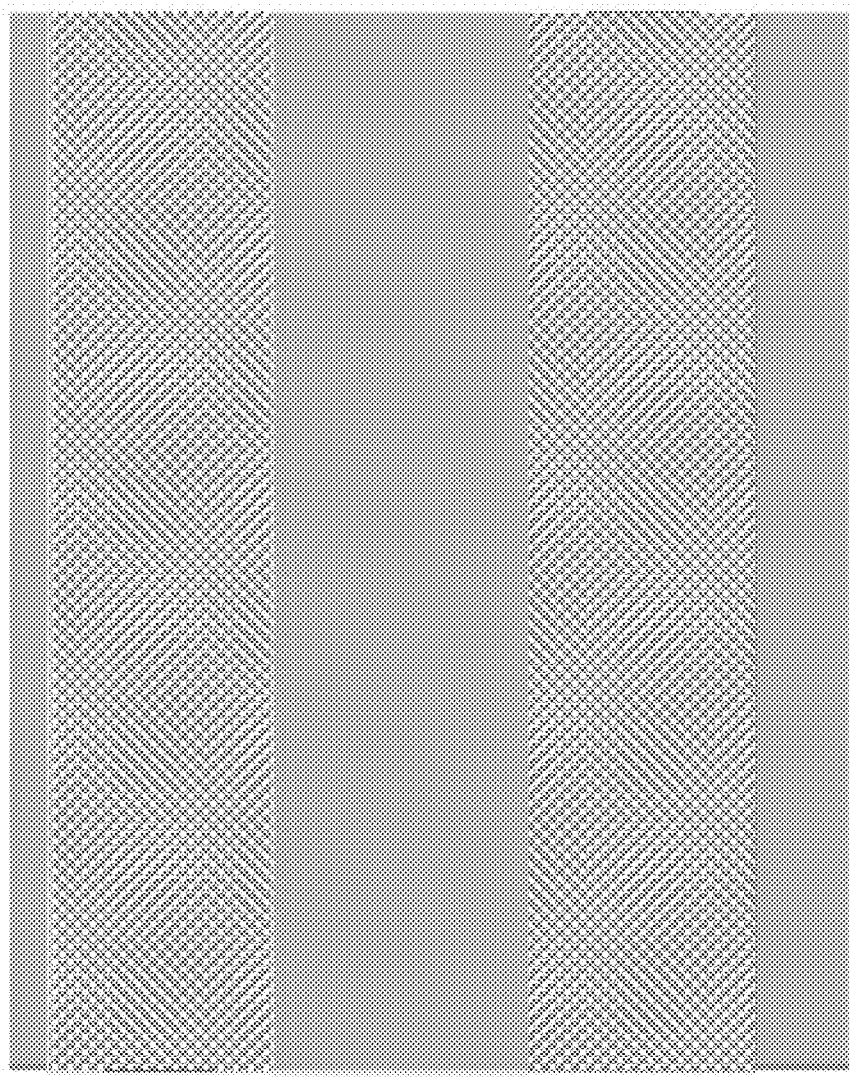
[Fig. 23A]
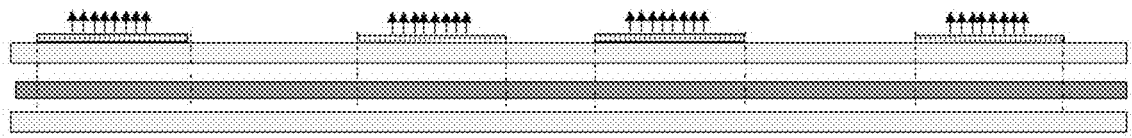

[Fig. 23B]
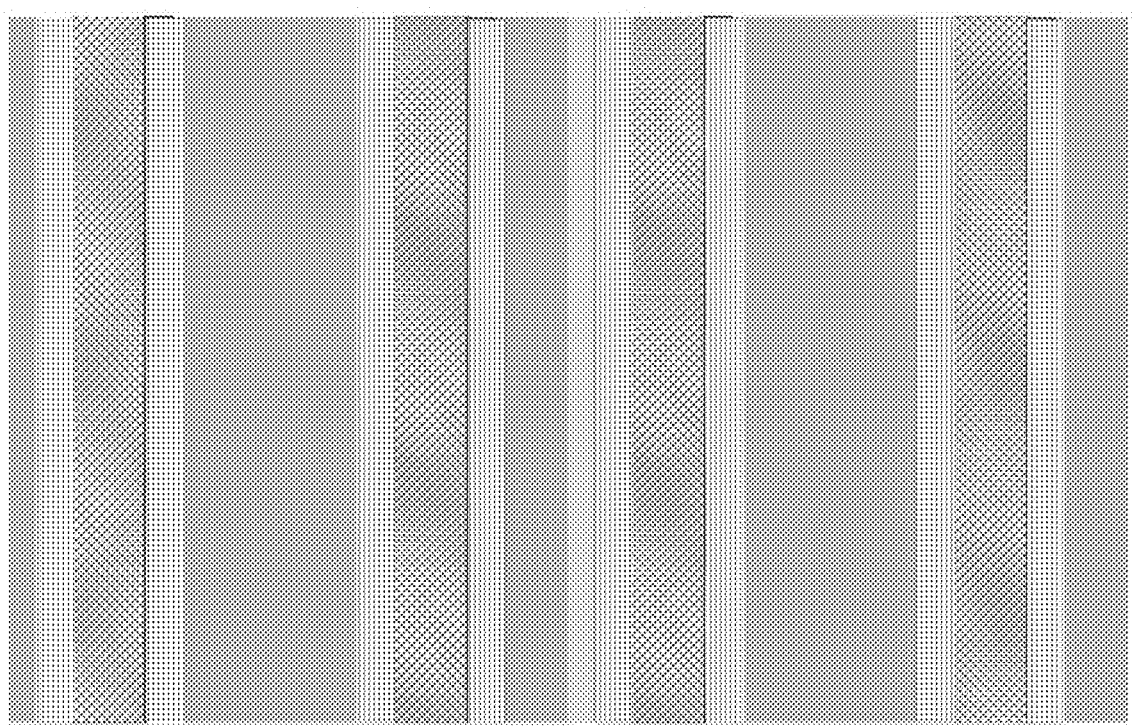
[Fig. 24]
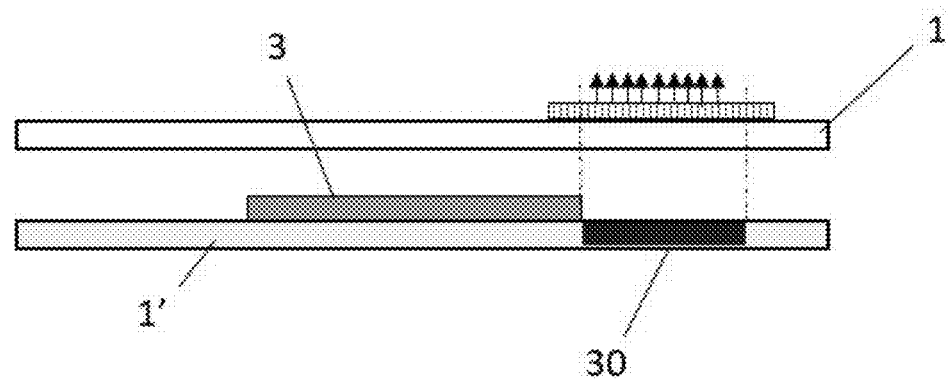

[Fig. 25]
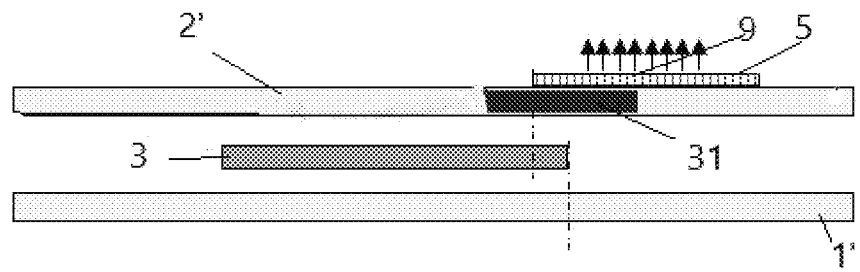
[Fig. 26]
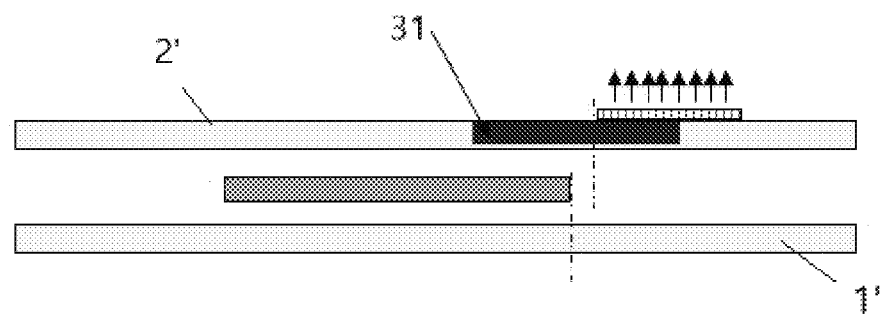
[Fig. 27]
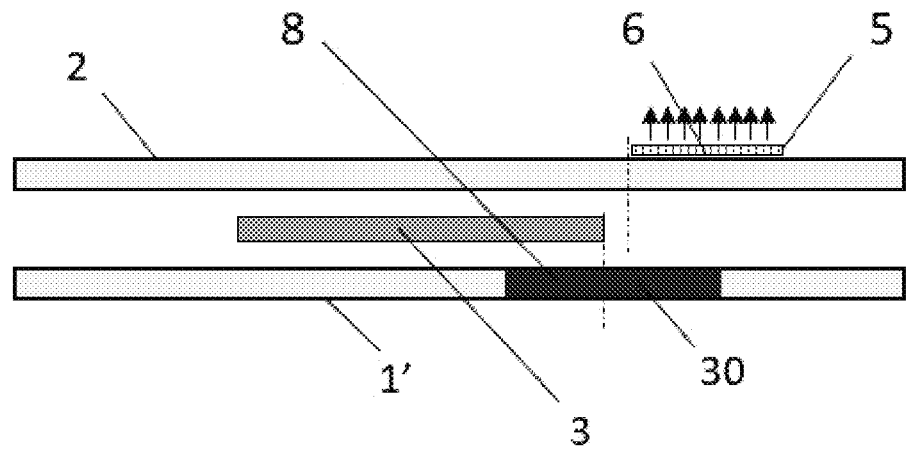

[Fig. 28]
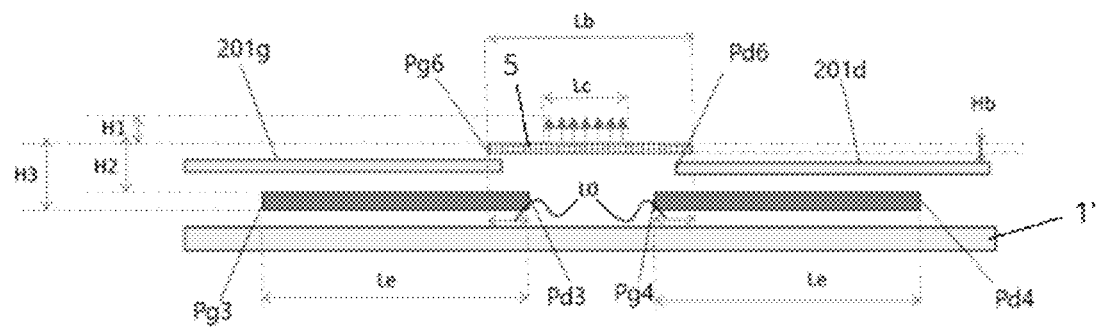
[Fig. 29]
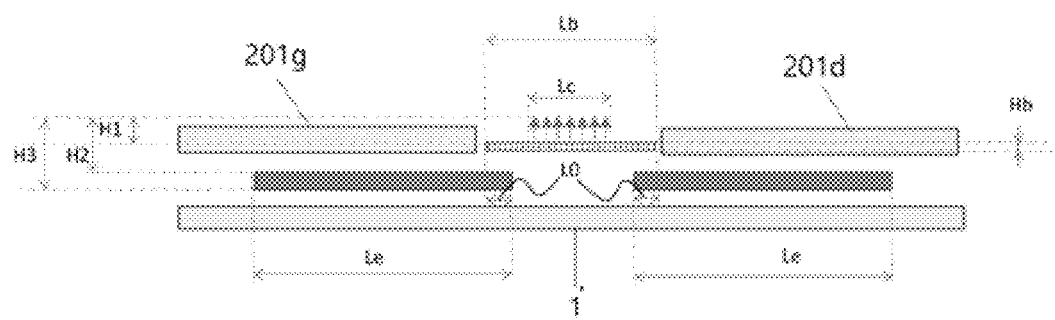
[Fig. 30]
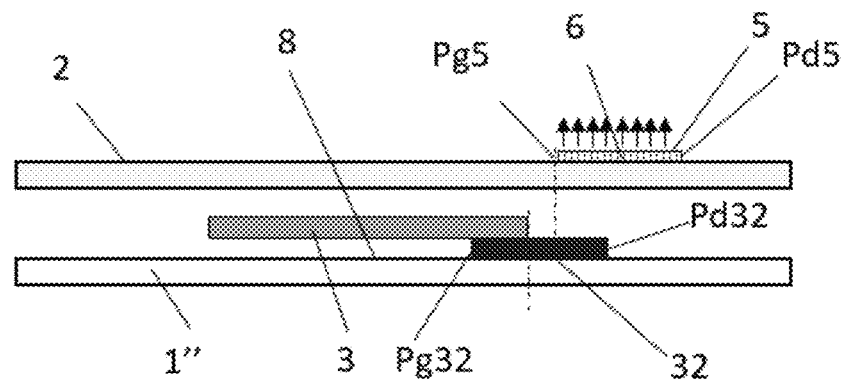

[Fig. 31]
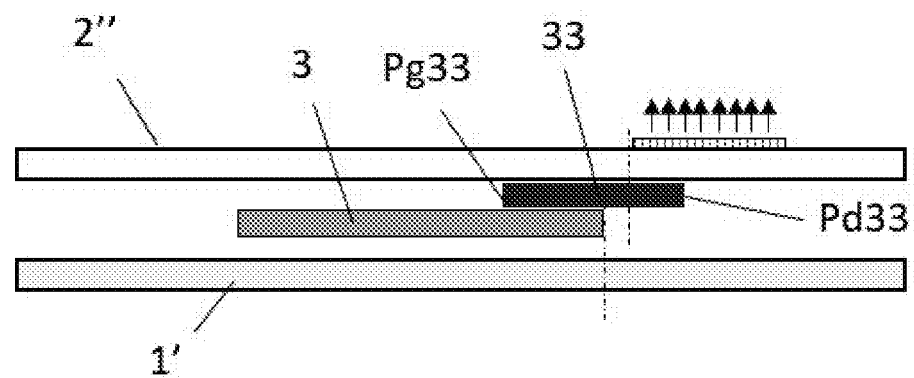
[Fig. 32]
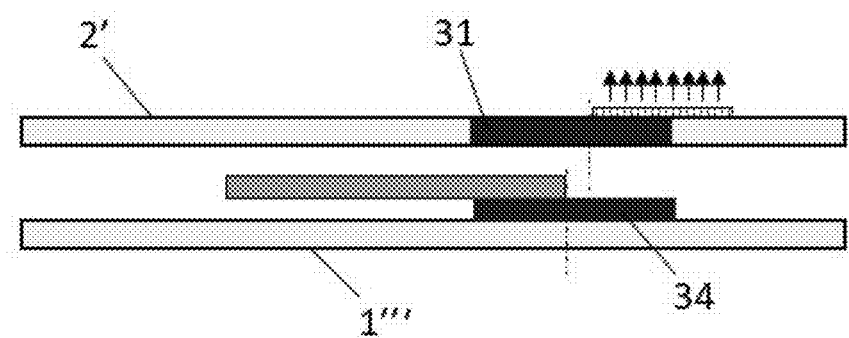

ELASTIC LAMINATE WITH HOOKS

TECHNICAL FIELD

The invention relates to an elastic laminate which is intended to be used in the field of hygiene, and in particular for nappies or adult incontinence pants, the laminate comprising an upper layer of nonwoven fabric extending in accordance with a given width corresponding to the direction CD (Cross Direction or Transverse Direction) and a large length corresponding to the unwinding direction during the manufacture of the laminate, referred to as the direction MD (Machine Direction), and at least one elastic film extending over a width that is less than or equal to the width of the at least one layer of nonwoven fabric, the upper face thereof being attached, for example by an adhesive, such as glue, or by thermal lamination, ultrasonic welding, or the like, to the lower face of the layer of nonwoven fabric, while hooks, intended to engage with loops originating from another part of the element comprising the laminate or another element, protrude from a region of the upper face of the upper layer of nonwoven fabric.

BACKGROUND

A laminate of this type is known for example from WO 2010/109087, in the name of the applicant.

Although this elastic laminate from the prior art has considerable advantages with respect to that which existed previously, it is desirable to improve it further, and in particular to increase the durability of the hooking capacity of the hooks, which tend to lose their effectiveness for hooking to the loops over time, for example in the case of a nappy as the nappy is worn and/or used, in particular being opened, then closed, and so on.

SUMMARY OF THE INVENTION

The present invention aims to overcome the drawbacks of the prior art by proposing an elastic laminate with hooks, of the type mentioned above, which can be manufactured on a larger scale and which, at the same time, exhibits greater durability of the hooking capacity of its hooks over the course of use of the hooks in hook-and-loop engagement for closing, for example, a nappy around a baby's waist.

According to one aspect of the invention, an elastic laminate with hooks is as defined in claim 1.

According to another aspect of the invention, an assembly forming an elastic laminate with hooks, comprising an elastic laminate and one or more webs with hooks which are arranged on top of the elastic laminate;
  the laminate comprising one or more layers of nonwoven fabric and one or more elastic films attached under the layer of nonwoven fabric or under at least one layer of nonwoven fabric,
  the or each layer of nonwoven fabric having either a constant rigidity, or being divided into at least two zones, one first zone in which the layer of nonwoven fabric has a first lowest rigidity, and at least one second zone in which zone or zones the layer of nonwoven fabric has a rigidity greater than the first rigidity,
  the web or each of the webs comprising a respective strip, in particular made of a thermoplastic material, from which hooks protrude;
  the layer or layers of nonwoven fabric possibly comprising one or more reinforcing elements in the form of one or more reinforcing strips, and/or one or more reinforced zones of one or more layers of nonwoven fabric forming one or more second zone(s) of one or more of the layers of nonwoven fabric;
in which:
  the or each web with hooks extends between respective side end points, left-hand and right-hand respectively;
  the or each reinforcing element extends between respective side end points, left-hand and right-hand respectively;
characterised in that
  the web or at least one web (5) with hooks is directly attached, at least in part, to a layer of nonwoven fabric having a constant rigidity, or to said first zone of a layer of nonwoven fabric, or to the elastic film, or to at least one elastic film;
  one (Pg6; Pd6) of the two side end points (Pg6, Pd6), left-hand and right-hand respectively, of the web or of the at least one web (5) with hooks is located vertically in line with a point of the or at least one elastic film; and/or
  one of the two side end points, left-hand and right-hand respectively, of the or at least one reinforcing element is located vertically in line with a point of the or at least one elastic film.

By thus providing for the formation of an overlap, by the web with hooks, of one of the two left-hand and right-hand lateral edges of the elastic film, resistance is improved in the region of the connection between the end edges of the web with hooks that are closest to the elastic film, thus also combatting, to a large extent, untimely delamination of the elastic film on account of the stresses exerted in order to position the hooks at a suitable location on the nappy, and/or due to the action of the hooks on opposing loops, for example in the case of a nappy, as the nappy is used over time, for example being opened, then closed, and so on, a longer durability of the hooking capacity of the elastic laminate with hooks is thus ensured.

Preferably, the elastic film or films extend in the direction CD over a width less than the width in the direction CD of the laminate.

In some cases, one or more elastic film(s) extend in the direction CD over a width less than or equal to the width of the upper layer or layers of nonwoven fabric, and/or the width of the upper layer or layers of nonwoven fabric is equal to the width in the direction CD of the laminate.

In other cases, one or more elastic film(s) extend in the direction CD over a width greater than the width of the upper layer or layers of nonwoven fabric, and/or the width of the upper layer or layers of nonwoven fabric is less than the width in the direction CD of the laminate.

Preferably, the other side end point, right-hand and left-hand respectively, of the or of the at least one web with hooks is not vertically in line with a point of the elastic film (or overhangs the elastic film). Thus, the amount of elastic in the region of the web with hooks is limited to just what is necessary to allow good anchorage of the film.

According to another favourable aspect of the invention, the elastic laminate with hooks, extending in width in a direction CD and in length in a direction MD, comprises:
  at least two upper layers of nonwoven fabric extending in width in the direction CD and in length in the direction MD, being spaced apart from one another in the direction CD, defining therebetween a nonwoven fabric gap;
  at least two elastic film(s) extending in the direction CD and in length in the direction MD, being spaced apart from one another so as to define therebetween an elastic film gap extending in the nonwoven fabric gap over a width that is less than this gap, each elastic film being attached by its upper face to the lower face of a respective upper layer of nonwoven fabric, in particular by interposition of an adhesive, for example glue, by thermal lamination, by ultrasonic welding, or the like; and a web with hooks, comprising a strip, in particular made of thermoplastic material, from which hooks protrude and which is attached, for example adhesively bonded, laminated or welded, or the like, on either side of said elastic film gap, to the upper faces of the elastic films by covering said elastic film gap, the hooks being in particular intended to engage with loops according to a hook-and-loop fastening system.

In particular, the web with hooks extends over the entire width or substantially over the entire width of the nonwoven fabric gap.

According to yet another favourable aspect of the invention, the elastic laminate with hooks, extending in width in a direction CD and in length in a direction MD, comprises:

at least two upper layers of nonwoven fabric extending in width in the direction CD and in length in the direction MD, being spaced apart from one another in the direction CD, defining therebetween a nonwoven fabric gap;

at least two elastic film(s) extending in the direction CD and in length in the direction MD, being spaced apart from one another so as to define therebetween an elastic film gap extending in the nonwoven fabric gap over a width that is less than this gap, each elastic film being attached by its upper face to the lower face of a respective upper layer of nonwoven fabric, in particular by interposition of an adhesive, for example glue, by thermal lamination, by ultrasonic welding, or the like; and a web with hooks, comprising a strip, in particular made of thermoplastic material, from which hooks protrude and which is attached, for example adhesively bonded, laminated or welded, or the like, on either side of said nonwoven fabric gap, to the upper faces of the two layers of nonwoven fabric, by covering said nonwoven fabric gap, the hooks being in particular intended to engage with loops according to a hook-and-loop fastening system.

According to yet another aspect of the invention, an elastic laminate with hooks comprises:

a nonwoven fabric element with hooks, which comprises at least one upper layer of nonwoven fabric extending in width in a direction CD and in length in a direction MD, in particular one or more upper layer(s) of nonwoven fabric and one lower layer of nonwoven fabric, and one or more webs with hooks, the hooks protruding from a region of an upper surface of the nonwoven fabric element with hooks, in particular from a region of the upper surface of the upper layer(s) of nonwoven fabric; and one or more elastic film(s) extending in the direction CD over a width that is less than or equal to the width of the element of nonwoven fabric with hooks, in particular to the width of the upper layer of nonwoven fabric, the or each elastic film being attached by its upper face to the lower face of the upper layer of nonwoven fabric, in particular by interposition of an adhesive, for example glue, by thermal lamination, by ultrasonic welding, or the like;

the nonwoven fabric element with hooks being divided into at least two types of zone, a first type of zone in which the nonwoven fabric with hooks has a first lowest rigidity, and a second type of zone in which the local rigidities of the nonwoven fabric element with hooks are all greater than the first rigidity, the or each zone of the second type, or zone of greater rigidities, extending in the direction CD between respective side end points of the zone of greater rigidities, left-hand and right-hand respectively, and is characterised in that one of the two side end points, left-hand and right-hand respectively, of the zone or one of the zones of greater rigidities is located vertically in line with a point of the or an elastic film.

Preferably, the elastic film or films extend in the direction CD over a width less than the width in the direction CD of the nonwoven fabric element with hooks.

According to a preferred embodiment, the elastic laminate, for example comprising the adhesive between the upper and lower layers of nonwoven fabric and between the upper and lower layers of nonwoven fabric, respectively, of the elastic film or films, the nonwoven fabric element with hooks consists (exclusively) of one or more upper layer(s) of nonwoven fabric extending in width in a direction CD and in length in a direction MD, and one or more web(s) with hooks, the or each web comprising a strip, in particular made of thermoplastic material, from which hooks protrude and which is attached, for example adhesively bonded, laminated or welded, or the like, onto the upper face of the upper layer(s) of nonwoven fabric or onto the upper face of the elastic film or films, the hooks being in particular intended to engage with loops according to a hook-and-loop fastening system.

According to another preferred embodiment, the elastic laminate, for example comprising the adhesive between the upper and lower layers of nonwoven fabric and between the upper and lower layers of nonwoven fabric, respectively, and the elastic film or films, the nonwoven fabric element with hooks consists (exclusively) of:

one or more upper layer(s) of nonwoven fabric, each extending in width in a direction CD and in length in a direction MD, one or more lower layer(s) of nonwoven fabric, each extending in width in a direction CD and in length in a direction MD, and one or more web(s) with hooks, the or each web comprising a strip, in particular made of thermoplastic material, from which hooks protrude and which is attached, for example adhesively bonded, laminated or welded, or the like, onto the upper face of the upper layer(s) of nonwoven fabric or onto the upper face of the elastic film or films, the hooks being in particular intended to engage with loops according to a hook-and-loop fastening system.

According to a preferred embodiment, the other side end point, right-hand and left-hand respectively, of the zone or of the at least one of the zones of greater rigidities is not vertically in line with a point of the elastic film (or overhangs the elastic film).

According to a favourable embodiment, one of the two side end points, left-hand and right-hand respectively, of the or of the at least one web with hooks is not vertically in line with a point of the zone or of the at least one of the zones of greater rigidities (or overhangs the zone or the at least one of the zones of greater rigidity).

According to another embodiment which is also favourable, one of the two side end points, left-hand and right-hand respectively, of the or of the at least one web with hooks is vertically in line with a point of the zone or of the at least one of the zones of greater rigidities.

According to another alternative which is also favourable, the other side end point, right-hand and left-hand respectively, of the web with hooks or of the at least one web with hooks is vertically in line with a point of the elastic film. Thus, the amount of elastic in the region of the web with hooks is at a maximum in order to ensure maximum anchorage and maximum coverage of the end of the elastic layer.

According to a preferred embodiment, the strip of the web with hooks is laminated to the upper layer of nonwoven fabric such that the strip comprises fibres and/or filaments of the layer of nonwoven fabric, and or fibres and/or filaments are encapsulated in the strip of the web with hooks.

According to an even more preferred embodiment of the invention, the or at least one upper layer of nonwoven fabric comprises a reinforced zone of the upper layer of nonwoven fabric, said reinforcement having been achieved for example by impregnating it with glue and/or by carrying out heat treatment, resulting in a local rigidification of the material of the layer of nonwoven fabric, in order to thus form a region inside the upper layer of nonwoven fabric which has a greater rigidity than the rest of the layer of nonwoven fabric.

According to a particularly preferred embodiment of the invention, it is preferable that, at the same time, the or a web with hooks, and the reinforced zone, overlap an end edge of the elastic film, each having an end point in line with a point of the elastic film.

Preferably, the opposite end points of the or the at least one web with hooks and the reinforced zone are not in line with the elastic film (or overhang the elastic film), i.e. are located outside the zone located above the elastic film.

Preferably, the or at least one web with hooks comprises a central region from which the hooks protrude, and at least one selvedge region, in particular two left-hand and right-hand side selvedge regions, from which hooks do not protrude, and one of the two selvedge regions comprises at least one point which is perpendicular to a side edge of the elastic film.

Preferably two selvedge regions are provided, and the other selvedge region and the central region are located outside the zone located above the elastic film.

Preferably, the central region of hooks comprises at least one point that is vertically in line with the reinforced zone such that the selvedge region or one of the two selvedge regions, and a part of the central region, are located above the reinforced zone.

Preferably two selvedge regions are provided, and the other of the two selvedge regions and the remainder of the central region are located outside the zone located above the reinforced zone.

According to a preferred embodiment, the or a web with hooks is arranged centrally on the upper face of the laminate, in particular of the upper layer of nonwoven fabric.

According to an advantageous embodiment, a lower layer of nonwoven fabric is provided, which is attached to the lower face of the elastic film or films.

According to an advantageous embodiment, the upper layer of nonwoven fabric and/or the lower layer of nonwoven fabric each has or have a basis weight of between 5 and 100 grams/m², in particular between 25 and 65 grams/m².

In particular, the lower layer of nonwoven fabric comprises a reinforced zone arranged under the web with hooks, preferably without being below the elastic film.

According to an advantageous embodiment, the strip of the web with hooks has a thickness of between 10 micrometres and 700 micrometres, in particular a thickness of between 40 micrometres and 120 micrometres.

According to an advantageous embodiment, the web with hooks may comprise rods and/or hooks.

According to an advantageous embodiment, the rods and/or hooks have a height of between 5 and 5,000 micrometres, more particularly between 5 and 2,000 micrometres, or even more particularly between 20 and 800 micrometres, or even more particularly between 30 and 350 micrometres, the height being measured according to a direction perpendicular to the upper face of the strip of the web with hooks.

According to an advantageous embodiment, the hooks and the strip are formed in one piece, being formed by extrusion.

According to an advantageous embodiment, the hooks and the strip are made of the same material, for example a thermoplastic material.

According to an advantageous embodiment, the hooks and the strip are made of at least two different thermoplastic materials.

The direction MD is also referred to as "machine direction" and refers to the unwinding direction of the laminate according to the invention. The direction CD is also referred to as "cross direction" and is perpendicular to the direction MD.

According to a favourable embodiment, the nonwoven fabric element with hooks is formed of an upper layer of nonwoven fabric extending in width in the direction CD and in length in the direction MD, and at least one web with hooks which protrude from a region of the upper surface of the upper layer of nonwoven fabric.

According to another favourable embodiment, the nonwoven fabric element with hooks is formed of an upper layer of nonwoven fabric extending in width in the direction CD and in length in the direction MD, a lower layer of nonwoven fabric extending in width in the direction CD and in length in the direction MD, and at least one web with hooks which protrudes from a region of the upper surface of the upper layer of nonwoven fabric, the elastic film or films being received inside the nonwoven fabric element with hooks, between the two upper and lower layers of nonwoven fabric.

The present invention also relates to an elastic tab with hooks, intended to be attached to a part, in particular rear, of a nappy, the tab comprising an elastic laminate according to the invention and/or being obtained by cutting out from an elastic laminate according to the invention.

In particular, the tab comprises a substantially rectangular base part and a tongue-shaped part which protrudes laterally from the base part.

Preferably, the tab is delimited by a cutting line in parallel with the direction MD and corresponding to one of the side edges of the laminate according to the invention, two cutting lines, lower and upper respectively, spaced apart from one another and in parallel with one another and extending in the direction CD, two intermediate cutting lines in parallel with the direction MD, two inclined cutting lines each extending from a respective intermediate line, being inclined with respect both to the direction CD and to the direction MD so as to converge towards one another, and an end cutting line in parallel with the direction MD, which interconnects the two inclined lines.

The base part is delimited by the cutting line in parallel with the direction MD, the two cutting lines, lower and upper respectively, spaced apart from one another and in parallel with one another and extending in the direction CD, and the virtual line extending between the two lower and upper cutting lines, in parallel with the direction MD and passing through the two intermediate cutting lines, while the tongue-shaped part is delimited by the part of the virtual line extending between the two intermediate lines, the two inclined lines, and the end line.

Preferably, the cut corresponding to the end cutting line is made substantially in the region of the end edge of the web with hooks, respectively of the zone of greater rigidities, while the cut corresponding to the intermediate lines is made substantially in the region of the end edge Pd6 of the web with hooks, respectively of the zone of greater rigidities, such that the entirety of the central region with hooks is located in the tongue-shaped part, and the majority of the elastic film or films is located in the base part, a part of the elastic film or films also encroaching on the tongue-shaped part.

Preferably, the end cutting line is made between 1 mm and 10 mm from the edge (inside the web with hooks, more particularly from 2 mm to 5 mm from the edge).

By extending in this way at a distance from the edge (on the inside), the elastic tabs thus comprise a portion of web with hooks which extends over the entire height of the elastic lug or tab, which has the effect of distributing the stress applied to the tongue in the form of sub-stresses in parallel therewith on the base part, in particular on the elastic film. Thus, the stresses applied to the elastic film, and in particular to the end of the elastic film, are distributed over the entire length in MD, making it possible to help reduce delamination of the elastic film.

The present invention also relates to a method for cutting a laminate according to the invention in order to obtain one or more elastic tabs with hooks according to the invention.

The present invention also relates to a nappy for a baby or adult incontinence pants comprising, in particular, an upper sheet (referred to as "topsheet"), a lower sheet (referred to as "backsheet"), and an absorbent core arranged between the two sheets, and at least one laminate according to the invention, in particular in order to form the hook tabs originating laterally from the rear waist of the nappy or incontinence pants such that the hooks engage with loops originating from the front face of the waist of the nappy, in order to achieve closure of the nappy or incontinence pants.

The present invention also relates to a roll comprising at least one laminate according to the invention, in particular wound onto itself, in particular in order to form, for example after cutting, hook tabs originating laterally from the rear waist of a nappy or incontinence pants such that the hooks engage with the loops originating from the front face of the waist of the nappy in order to achieve closure of the nappy or incontinence pants.

BRIEF DESCRIPTION OF THE DRAWINGS

By way of example, a plurality of embodiments of the invention will now be described, with reference to the drawings, in which:

FIG. 1A is an exploded cross-section CD of a laminate according to a first embodiment of the invention;

FIG. 1B is a plan view of a part of the laminate of FIG. 1A, further comprising dotted lines in order to explain the manner in which the laminate of FIG. 1A can be cut in order to form tabs with hooks which are intended to be used, for example, in nappies;

FIG. 2 is a view identical to that of FIG. 1A, on a slightly larger scale, showing some distances defined in the description;

FIG. 3A is a cross-section CD of a laminate according to another embodiment of the invention;

FIG. 3B is a plan view of a part of the laminate of FIG. 3A, further comprising dotted lines showing the manner in which the laminate can be cut in order to form tabs with hooks which are intended to be used, for example, in nappies;

FIG. 4A is a cross-section CD of a laminate according to another embodiment of the invention;

FIG. 4B is a plan view of a part of the laminate of FIG. 4A, further comprising dotted lines showing the manner in which the laminate can be cut in order to form tabs with hooks which are intended to be used, for example, in nappies or the like;

FIG. 5A is a cross-section CD of a laminate according to another embodiment of the invention;

FIG. 5B is a plan view of a part of the laminate of FIG. 5A;

FIG. 6A is a cross-section CD of a laminate according to another embodiment of the invention;

FIG. 6B is a plan view of a part of the laminate of FIG. 6A;

FIG. 7A is a cross-section CD of a laminate according to another embodiment of the invention;

FIG. 7B is a plan view of a part of the laminate of FIG. 7A;

FIG. 8A is a cross-section CD of a laminate according to another embodiment of the invention;

FIG. 8B is a plan view of a part of the laminate of FIG. 8A;

FIG. 9A is a cross-section CD of a laminate according to another embodiment of the invention;

FIG. 9B is a plan view of a part of the laminate of FIG. 9A, further comprising dotted lines showing the manner in which the laminate can be cut in order to form tabs with hooks which are intended to be used, for example, in nappies or the like;

FIG. 10A is a cross-section CD of a laminate according to another embodiment of the invention;

FIG. 10B is a plan view of a part of the laminate of FIG. 10A;

FIG. 11A is a cross-section CD of a laminate according to another embodiment of the invention;

FIG. 11B is a plan view of a part of the laminate of FIG. 11A;

FIG. 12A is a cross-section CD of a laminate according to another embodiment of the invention;

FIG. 12B is a plan view of a part of the laminate of FIG. 12A;

FIG. 13A is a cross-section CD of a laminate according to another embodiment of the invention;

FIG. 13B is a plan view of a part of the laminate of FIG. 13A, further comprising dotted lines showing the manner in which the laminate can be cut in order to form tabs with hooks which are intended to be used, for example, in nappies or the like;

FIG. 14A is a cross-section CD of a laminate according to another embodiment of the invention;

FIG. 14B is a plan view of a part of the laminate of FIG. 14A, further comprising dotted lines showing the manner in which the laminate can be cut in order to form tabs with hooks which are intended to be used, for example, in nappies or the like;

FIG. 15A is a cross-section CD of a laminate according to another embodiment of the invention;

FIG. 15B is a plan view of a part of the laminate of FIG. 15A, further comprising dotted lines showing the manner in which the laminate can be cut in order to form tabs with hooks which are intended to be used, for example, in nappies or the like;

FIG. 16A is a cross-section CD of a laminate according to another embodiment of the invention;

FIG. 16B is a plan view of a part of the laminate of FIG. 16A;

FIG. 17A is a cross-section CD of a laminate according to another embodiment of the invention;

FIG. 17B is a plan view of a part of the laminate of FIG. 17A;

FIG. 18A is a cross-section CD of a laminate according to another embodiment of the invention;

FIG. 18B is a plan view of a part of the laminate of FIG. 18A;

FIG. 19A is a cross-section CD of a laminate according to another embodiment of the invention;

FIG. 19B is a plan view of a part of the laminate of FIG. 19A;

FIG. 20A is a cross-section CD of a laminate according to another embodiment of the invention;

FIG. 20B is a plan view of a part of the laminate of FIG. 20A, further comprising dotted lines showing the manner in which the laminate can be cut in order to form tabs with hooks which are intended to be used, for example, in nappies or the like;

FIG. 21A is a cross-section CD of a laminate according to another embodiment of the invention;

FIG. 21B is a plan view of a part of the laminate of FIG. 21A;

FIG. 22A is a cross-section CD of a laminate according to another embodiment of the invention;

FIG. 22B is a plan view of a part of the laminate of FIG. 22A;

FIG. 23A is a cross-section CD of a laminate according to another embodiment of the invention;

FIG. 23B is a plan view of a part of the laminate of FIG. 23A;

FIG. 24 is a cross-section CD of a laminate according to yet another embodiment of the invention;

FIG. 25 is a cross-section CD of a laminate according to yet another embodiment of the invention;

FIG. 26 is a cross-section CD of a laminate according to an embodiment of the invention;

FIG. 27 is a cross-section CD of a laminate according to another embodiment of the invention;

FIG. 28 is a cross-section CD of a laminate according to yet another embodiment of the invention;

FIG. 29 is a cross-section CD of a laminate according to yet another embodiment of the invention;

FIG. 30 is a cross-section CD of a laminate according to yet another embodiment of the invention;

FIG. 31 is a cross-section CD of a laminate according to yet another embodiment of the invention; and FIG. 32 is a cross-section CD of a laminate according to yet another embodiment of the invention.

FIGS. 1A and 1B show a first embodiment of the invention.

DETAILED DESCRIPTION OF THE INVENTION

The elastic laminate, shown there in cross-section in FIG. 1A, according to the direction CD, extends perpendicularly to the figure over a very significant length (the laminate is intended to be unwound), and over a given width L of the laminate. The elastic laminate with hooks comprises an elastic laminate which comprises a lower layer 1 of nonwoven fabric, an upper layer 2 of nonwoven fabric and, interposed between the two upper and lower layers of nonwoven fabric, two elastic films 3 and 4, left-hand and right-hand, which are each of a width Le that is smaller than the width L of the laminate, the sum of the two widths (in this case the two films have the same width Le, but could have different widths) also being less than the width L of the laminate. The elastic laminate with hooks also comprises a web 5 with hooks which is arranged centrally on the upper layer 2 of nonwoven fabric and is formed by a base strip 6 from which hooks 10 protrude. The upper layer of nonwoven fabric 2 extends in the direction CD over the entire width CD of the laminate. The rigidity of the layer 2 of nonwoven fabric is constant over its entire width in the direction CD. The lower layer of nonwoven fabric 1 extends in the direction CD over the entire width CD of the laminate. The rigidity of the layer 1 of nonwoven fabric is constant over its entire width in the direction CD.

A nonwoven fabric element 8 with hooks is thus formed by the assembly formed by the lower layer 1 of nonwoven fabric, the upper layer 2 of nonwoven fabric, and the web 5 with hooks, as well as optional layers of adhesive or glue between the two layers of nonwoven fabric, between the upper layer of nonwoven fabric and the web with hooks, and between the layers of nonwoven fabric and the elastic film.

The two elastic films 3 and 4 are attached, respectively on the top and on the bottom, to the two layers 1 and 2 of nonwoven fabric, for example by means of glue, in particular strips of glue which are not necessarily continuous and may in particular be implemented in the form of glue dots or glue lines or by hot lamination. Furthermore, it is also possible to provide glue and/or optionally additional reinforcing elements (not shown in the figures) between the two lower and upper nonwoven fabrics 1 and 2, outside the two elastic films.

The elastic film 3 extends between two left-hand and right-hand end edges which, in FIG. 1A, in the cross-section CD, form two end points Pg3 and Pd3, left-hand and right-hand respectively, of the elastic film 3. In the same way, the elastic film 4 extends between two left-hand and right-hand end edges which, in FIG. 1A, in the cross-section CD, form two end points Pg4 and Pd4, left-hand and right-hand respectively, of the elastic film 4. An elastic film gap, extending between the points Pd3 and Pg4, is defined between the two elastic films 3 and 4.

The base strip 6 of the web 5 with hooks extends between two left-hand and right-hand end edges which, in the figure, in the cross-section CD, form two end points Pg6 and Pd6, left-hand and right-hand respectively, of the base strip, which also form the two end points Pg5 and Pd5 of the web 5 with hooks.

The base strip 6 comprises two selvedge regions, left-hand and right-hand, 7g and 7d, from which no hooks protrude, and a central region 9 from which hooks 10 protrude. The central region 9 with hooks is delimited by two left-hand and right-hand end edges which, in FIG. 1A, in the cross-section CD, form two end points Pg10 and Pd10, left-hand and right-hand respectively, of the central region 9.

The web 5 with hooks is attached by means of gluing, thermal lamination, ultrasonic welding, or the like, of the lower face of the base strip 6 to the upper face of the upper layer 2 of nonwoven fabric.

For the nonwoven fabric element 8 with hooks, it is possible to define a zone of first rigidity, which corresponds to the rigidity of the two layers 2 of nonwoven fabric taken individually together with the adhesive therebetween, i.e. in the two regions to the left-hand and right-hand side of the web 5 with hooks, which extend on the one hand from the left-hand end edge of the layer 2 of nonwoven fabric as far as the left-hand edge Pg6 of the base strip 6, and on the other hand from the right-hand edge Pd6 of the base strip 6 as far as the right-hand end edge of the nonwoven fabric layer 2.

It is also possible to define a zone of greater rigidities which extends between the end edges Pg6 and Pd6 and which simultaneously includes the part of the layer 2 of nonwoven fabric that is located below the web 5 with hooks. In the region of the central region 9 with hooks, the rigidity of the zone of greater rigidities is greater, compared with the first rigidity, than the rigidity in the region of the selvedges 7g and 7d without hooks. Nevertheless, in these two zones of different rigidities, each rigidity is, however, greater than the first rigidity, which corresponds to the lowest rigidity that can be defined for a zone of the nonwoven fabric element 8.

Viewed in cross-section CD, the web 5 with hooks is located on top of the elastic laminate and above the two elastic films 3 and 4, and the end edge or point Pg6 of the web 5 with hooks is located vertically in line with the elastic film 3, while the end edge or point Pd6 of the web with hooks is not vertically in line with the elastic film 3 (or overhangs said film), and in particular is vertically in line with a point that is at a distance, in the transverse direction, from the elastic film 3. Thus, the web 5 with hooks overlaps the right-hand end point Pd3 of the elastic film 3.

Viewed in cross-section CD, the end edge or point Pd6 of the web 5 with hooks is located vertically in line with the elastic film 4, while the end edge or point Pg6 of the web 5 with hooks is not vertically in line with the elastic film 4 (or overhangs said film), in particular is vertically in line with a point that is at a distance, in the transverse direction, from the elastic film 4. Thus, the web 5 with hooks overlaps the left-hand end point Pg4 of the elastic film 4.

Viewed in cross-section CD, the end edge or point Pg6 of the zone of greater rigidities of the nonwoven fabric element 8 with hooks is located vertically in line with the elastic film 3, while the end edge or point Pd6 of the zone of greater rigidity is not vertically in line with the elastic film 3 (or overhangs said film), and in particular is vertically in line with a point that is at a distance, in the transverse direction, from the elastic film 3. Thus, the zone of greater rigidities of the nonwoven fabric element 8 overlaps the right-hand end point Pd3 of the elastic film 3.

Viewed in cross-section CD, the end edge or point Pd6 of the zone of greater rigidities of the nonwoven fabric element 8 with hooks is located vertically in line with the elastic film 4, while the end edge or point Pg6 of the zone of greatest rigidity is not vertically in line with the elastic film 4 (or overhangs said film), and in particular is vertically in line with a point that is at a distance, in the transverse direction, from the elastic film 4. Thus, the zone of greater rigidities of the nonwoven fabric element 8 overlaps the left-hand end point Pg4 of the elastic film 4.

In contrast, in this embodiment shown, the central region 9 with hooks does not overlap any point or edge of the two elastic films 3 and 4, remaining entirely in line with the zone extending between the two left-hand and right-hand elastic films 3 and 4.

FIG. 1B is a plan view of the laminate over part of its length. Dotted lines show cutting lines for cutting the laminate into a succession of tabs 11g and 11d with hooks, left-hand and right-hand, respectively.

Said tabs with hooks, also referred to as lugs, are in particular intended to be attached to the edges, left-hand and right-hand respectively, of the rear part of a nappy or the like such that the hooks protrude laterally therefrom in order to engage with elements, in particular loops, formed in the front part of the nappy or the like (in particular adult incontinence pants), in order to ensure closure, by means of a hook-and-loop fastening system, of the nappy or the like.

Each tab 11g, 11d comprises a substantially rectangular base part 12g, 12d and a tongue-shaped part 13g, 13d which protrudes laterally from the base part 12g, 12d.

Each tab is delimited by a cutting line 14g, 14d in parallel with the direction MD and corresponding to one of the side edges of the laminate of FIG. 1A, two cutting lines 15g, 15d and 16g, 16d, lower and upper respectively, spaced apart from one another and in parallel with one another and extending in the direction CD, two intermediate cutting lines 17g, 17d and 18g, 18d in parallel with the direction MD, two inclined cutting lines 19g, 19d and 20g, 20d each extending from a respective intermediate line 17g, 17d and 18g, 18d, being inclined with respect both to the direction CD and to the direction MD so as to converge towards one another, and an end cutting line 21g, 21d in parallel with the direction MD, which interconnects the two inclined lines 19g, 19d and 20g, 20d.

The two intermediate cutting lines 17g, 17d and 18g, 18d have different lengths (according to the direction MD), but could also have the same length. In the same way, the angles of inclination of the two inclined lines are equal in terms of absolute value (being of opposing signs), but could have different values.

The substantially rectangular base part 12g, 12d is delimited by the cutting line 14g, 14d in parallel with the direction MD, the two cutting lines 15g, 15d and 16g, 16d, lower and upper respectively, spaced apart from one another and in parallel with one another and extending in the direction CD, and the virtual line extending between the two lower and upper cutting lines 15g, 15d and 16g, 16d, in parallel with the direction MD and passing through the two intermediate cutting lines 17g, 17d and 18g, 18d.

The tongue-shaped part 13g, 13d is delimited by the part of the virtual line extending between the two intermediate lines 17g, 17d and 18g, 18d, the two inclined lines 19g, 19d and 20g, 20d, and the end line 21g, 21d.

The cut along the lines 21g, 21d is made substantially in the region of the end edge of the web with hooks, while the cut corresponding to the intermediate lines is made substantially in the region of the end edge Pd6 of the web with hooks such that the entirety of the central region with hooks is located in the tongue-shaped part, and the majority of the elastic film or films is located in the base part, a part of the elastic film or films also encroaching on the tongue-shaped part.

Preferably, the end cutting lines 21g, 21d extend between 1 mm and 10 mm from the edge, inside the web with hooks, more particularly from 2 mm to 5 mm from the edge. By extending in this way at a distance from the edge, on the inside, the elastic tabs thus comprise a portion of the web 5 with hooks which extends over the entire height of the elastic lug or tab.

The cut corresponding to the end cutting line 20g, 20d is made substantially in the region of the end edge Pg6 of the zone having the greatest rigidity (which, in the embodiment described here, also corresponds to the left-hand end edge of the web 5 with hooks or the base strip 6 thereof), while the cut corresponding to the intermediate lines 17g, 17d and 18g, 18d is made substantially in the region of the end edge Pd6 of the zone having the greatest rigidity (which, in the embodiment described here, also corresponds to the right-hand end edge of the web 5 with hooks or the base strip 6 thereof).

Thus, the entirety of the central region 9 with hooks is located in the tongue-shaped part 13g, 13d, and the majority of the elastic films 3 and 4 is located in the respective base part 12d, 12g. However, due to the overlap described above, a part of the elastic films 3 and 4 encroaches into the tongue-shaped part 13g, 13d.

Some dimensions are defined in FIG. 2. The vertical distances, referred to by H, are measured perpendicularly to the upper face of the laminate (i.e. perpendicularly to the directions CD and MD), and the width distances, referred to by L, are measured according to the direction CD. The distance (H2) between the upper face of the base strip 6 (with hooks/rods) and the upper face of each elastic film 3 and 4 is less than the distance (H3−Hb) between the lower face of the base strip 6 and the lower face of each elastic film 3 and 4 (i.e. H2<H3−Hb) and/or the distance (H2−Hb) between the lower face of the base strip 6 (with hooks/rods) and the upper face of each elastic film 3 and 4 is less than the distance (H3−Hb) between the lower face of the base strip 6 and the lower face of each elastic film 3 and 4 (i.e. H2−Hb<H3−Hb). In the case of a ratio of this kind, the base strip 6 is arranged in a first space defined by two parallel planes (formed by the upper face and the lower face of the base), and each elastic film 3 and 4 is arranged in a second space defined by two other parallel planes (formed by the upper face and the lower face of each elastic film 3 and 4); the first and second spaces are separate.

The width of the overlap Lo is between 0.5 and 15 mm, in particular between 1 and 7 mm, more particularly between 1 and 5 mm.

| If it is considered that 13 mm =< Lb =< 60 mm | | |
| --- | --- | --- |
| | Lb | |
| Lo | 13 | 60 |
| 0.5 | 3.8% | 0.8% |
| 15 | 115.4% | 25.0% |
| Thus 0.8% * Lb <= L0 <= 116% * Lb | | |
| | Lb | |
| Lo | 13 | 60 |
| 1 | 7.7% | 1.7% |
| 7 | 53.8% | 11.7% |
| In particular, 1.7% * Lb <= L0 <= 54% * Lb | | |

The web with hooks may comprise rods and/or hooks. The rods and/or hooks have a height of between 5 and 5,000 micrometres, more particularly between 5 and 2,000 micrometres, or even more particularly between 20 and 800 micrometres, the height being measured according to a direction perpendicular to the upper face of the strip of the web with hooks.

A nonwoven fabric is intended to mean a product obtained following formation of a web of fibres and/or filaments that have been consolidated. The consolidation may be mechanical, chemical or thermal, and results in the presence of bonds between the fibres and/or the filaments. This consolidation may be direct, i.e. performed directly between the fibres and/or the filaments by means of welding, or it may be indirect, i.e. by means of an intermediate layer between the fibres and/or the filaments, for example a layer of adhesive or a layer of binder. The term "nonwoven fabric" relates to a structure in the form of a tape or web of fibres and/or filaments which are interlaced in a non-uniform or irregular manner, or at random. A nonwoven fabric may have a single layer structure or a structure comprising a plurality of layers. A nonwoven fabric may also be connected to another material in order to form a laminate. A nonwoven fabric may be made from different synthetic and/or natural materials. The natural materials, by way of example, are cellulose fibres such as cotton, jute, linen or the like, and may also include recycled cellulose fibres, such as rayon or viscose. The natural fibres for a nonwoven fabric material may be prepared by using various processes, such as carding. Synthetic materials, by way of example but without restriction thereto, include synthetic thermoplastic polymers, which are known to form fibres which include, without restriction thereto, the polyolefins, for example polyethylene, polypropylene, polybutylene, and the like; polyamide, for example polyamide 6, polyamide 6.6, polyamide 10, polyamide 12, and the like; polyesters, for example polyethylene terephthalates, polybutylene terephthalates, polylactic acids, and the like, polycarbonates, polystyrenes, thermoplastic elastomers, vinyl polymers, polyurethanes, and mixtures and co-polymers thereof. By way of example, the nonwoven fabric may be a nonwoven fabric of the spunbonded, spunmelt, carded thermobonded, spunlace (carded nonwoven fabric consolidated by hydroentangling), SMS, SMMS, SS, SSS, SSMMS, SSMMMS, Air through, or the like.

By way of non-limiting examples for an elastomer material, the following can be cited: styrene/isoprene (SI), styrene/isoprene/styrene (SIS), styrene/butadiene/styrene (SBS), styrene-ethylene/butylene-styrene (SEBS), styrene-ethylene/propylene-styrene (SEPS) copolymers, or SIBS. Mixtures of these elastomers with one another or with non-elastomers which modify some characteristics other than elasticity may also be considered. For example up to 50% by mass, but preferably less than 30% by mass, of polymer may be added in order to modify some characteristics of the base materials (elasticity, resistance to heat, processability, resistance to UV, colouring, etc.), such as polystyrenes or poly a-methyl-styrene, epoxy polyesters, polyolefins, for example polyethylenes or some ethylene/vinyl acetates, preferably those having higher molar masses.

The elastomer material may in particular be a styrene-isoprene-styrene, available for example from the company Kraton Polymers, under the name KRATON D (registered trademark), or from the company DEXCO POLYMERS LP under the name VECTOR SBC 4211 (registered trademark). It is also possible to use TPE (thermoplastic elastomer) materials, in particular a thermoplastic elastomer of polyurethane, in particular PELLETHANE (registered trademark) 2102-75A from the company The Dow Chemical Company. It is also possible to use a styrene-butadiene-styrene, in particular KRATON D-2122 (registered trademark) from the company Kraton Polymers, or VECTOR SBC 4461 (registered trademark) from the company Dexco Polymers LP. It is also possible to use a styrene-ethylene/butylene, in particular KRATON G-2832 (registered trademark) from the company Kraton Polymers, or a styrene-ethylene-butylene-styrene (SEBaS) copolymer sequence, in particular KRATON (registered trademark) G2703.

Without being exhaustive, the list can be supplemented by the use of all hydrogenated polyisoprene polymers such as styrene-ethylene-propylene-styrene (SEPS), styrene-ethylene-propylene-styrene-ethylene-ethylene-propylene (SEP-SEP), hydrogenated polybutadiene polymers such as styrene-ethylene-butylene-styrene (SEBS), styrene-ethylenebutylene-styrene-ethylene-ethylene-butylene-ethylene-butylene-butylene (SEBSEB), styrene-butadiene-styrene (SBS), styrene-isoprene-styrene (SIS), styrene-isoprene-butadiene-styrene (SIBS), hydrogenated polyisoprene/butadiene polymer such as styrene-ethylene-ethylene-ethylene-epropylene-styrene (SEEPS), and hydrogenated vinyl-polyisoprene/hydrogenated polyisoprene/polyisoprene/polystyrene triblock polymers, such as HYBRAR 7311, which are commercially available (Kuraray America, Inc., Houston, Tex.), and combinations thereof.

Block polymer configurations such as diblock, triblock, multiblock, multiblock, star and radial are also envisaged in this disclosure. In some cases, sequenced copolymers of or higher molar masses may be desirable. Sequenced copolymers are available from Kraton Polymers U.S. LLC of Houston, Tex. under the names, for example, Kraton MD6716, Kraton D1102, Kraton SIBS D1102, Kraton D1184, Kraton FG1901 and Kraton FG1924, and Septon Company of America, Pasadena, Tex. under the names Septon 8007, Septon V9827 and Septon 9618. Dynasol Spain is another possible provider of these polymers. In particular, the triblock polymer Kraton MD6716 SEBS is particularly suitable for the present disclosure.

It is also possible to use an isooctyl acrylate and acrylic acid copolymer, according to monomer ratios of 90/10, which is a thermoplastic having physical cross-linking in the absence of a cross-linking agent. It is also possible to use a polyamide polyester copolymer sequence PEBAX (registered trademark) 2533 from the company Arkema.

Other possible materials are polyolefin polymers, mainly ethylene and/or propylene copolymers, having elastomer characteristics, in particular originating from metallocene catalysis, such as VISTAMAXX VM-1120 (registered trademark), available from the company Exxon Mobil Chemical, or indeed rubber-loaded polymers, such as Santoprene loaded with EPDM.

Examples of thermoplastic elastomers based on polyolefins, which can be used in the elastomer film layers, include, inter alia, a crystalline polyolefin, for example a homopolymer or a copolymer of an alpha-olefin having 1 to 20 carbon atoms, and comprising 1 to 12 carbon atoms.

The homopolymers and the copolymers described below are examples of crystalline polyolefins.
  (1) Ethylene homopolymer. The ethylene homopolymer may be prepared by any of the low-pressure and high-pressure processes.
  (2) Ethylene copolymers, and no more than 10 mol % alpha-olefins other than ethylene, or vinylic monomers such as vinyl acetate and ethyl acrylate; for example, the ethylene octene copolymer, available under the trademarks Engage 8407 or Engage 8842 (Dow Chemical, Houston, Tex.).
  (3) Propylene homopolymer; examples include the polypropylene impact copolymer PP7035E4 and the polypropylene random copolymer PP9574E6 (Exxon Mobil, Houston, Tex.).
  (4) Any propylene copolymers, and no more than 10 mol % alpha-olefins-olefins other than propylene.
  (5) Sequenced propylene copolymers, and no more than 30 mol % alpha-olefins other than propylene.
  (6) Butene-1-butene homopolymer.
  (7) Any 1-butene copolymers, and no more than 10 mol % alpha-olefins-olefins other than 1-butene.
  (8) 4-methyl-1-pentene homopolymer, 4-methyl-1-pentene homopolymer.
  (9) Any 4-methyl-1-pentene copolymers, and no more than 20 mol % alpha-olefins other than 4-methyl-1-pentene.

The alpha-olefins include, for example, ethylene, propylene, butene-1, 4-methyl-1pentene, 1-hexene, and 1-octene.

The polyolefin-based thermoplastic elastomers that are commercially available and are intended to be used in the elastomer film layers include VISTAMAXX™ (polypropylene-based elastomer, available from ExxonMobil Chemical, Houston, Tex.), INFUSE™ (sequenced olefin copolymers, available from Dow Chemical Company, Midland, Michigan), VERSIFY™ (propylene-ethylene copolymers) such as VERSIFY™ 4200 and VERSIFY™ 4300 (Dow Chemical Company, Midland, Michigan), ENGAGE™ (ethylene octane copolymer, available from Dow Chemical, Houston, Tex.) and NOTIO 0040 and NOTIO 3560 (available from Mitsui Chemical (USA), New York, N.Y.), Adflex X100 G (available from Lyondellbasell).

In a particularly suitable embodiment, the polyolefin-based thermoplastic elastomer is VISTAMAXX™ 6102FL or VISTAMAXX 7050 FLX (available from ExxonMobil Chemical, Houston, Tex.). The reference "™" for registered trademarks corresponds to "Trade Mark".

In another case, the thermoplastic elastomer may be a thermoplastic ester/ether elastomer, or thermoplastic polyurethanes.

An elastomer material means a material which can be stretched without breaking under the effect of a stretching force exerted according to a given direction, and which can substantially return to its initial shape and dimensions after this stretching force is relaxed. This is for example a film which retains a residual deformation or set following elongation and relaxation (residual deformation also referred to as "permanent set" or "SET") that is less than or equal to 30%, preferably less than or equal to 20%, yet more preferably less than or equal to 10%, of the initial dimension thereof (prior to elongation) for an extension of 100% of the initial dimension thereof, at ambient temperature (23° C.—degrees Celsius). The elastomer material may be a thermoplastic elastomer material, in particular a physically cross-linked thermoplastic elastomer material, such as those described in the present disclosure, or a chemically cross-linked thermoplastic elastomer material.

By way of example, the list of plastics materials: LLDPE (Linear Low Density PolyEthylene), LDPE (Low Density PolyEthylene), m-PE (Metallocene PolyEthylene), HDPE (High Density PolyEthylene), EVA (Ethylene-Vinyl Acetate) and PP (Polypropylene), TPE of the Adflex and Vistamaxx type, having a monomodal or multimodal (for example bimodal) distribution of molar masses, in particular a composition comprising LLDPE and a plastomer, in particular a polyethylene-based plastomer. It would also be possible to use polyamide (PA), polylactic acid (PLA), polyhydroxyalcanoates (PHA), polyhydroxybutyrate (PHB), poly(ε-caprolactone) (PCL), Poly(glycolic acid) (PGA), polysuccinates (like: poly(ethylene succinate) (PESu), poly(propylene succinate) (PPSu), poly(butylene succinate) (PBSu)), polybutylene adipate terephtalate (PBAT), PVOH, PBS. The plastics materials may be combined in order to form mixtures. Mineral and/or organic loads, in the form of powder and/or fibres, for example up to 50% by mass, but preferably less than 30% by mass, may be incorporated into the plastics materials in order to modify some characteristics of the base materials (homogeneity, elasticity, resistance to heat, resistance to UV, colouring, processability, etc.).

Various systems and methods that are compatible with the present disclosure are described in the patent applications FR 16 53866, FR 16 53870, FR 16 53872, FR 16 53873, FR 16 53888, FR 16 53894 and FR 16 53897.

FIGS. 3A to 23A, and 3B to 23B, show other embodiments of the invention. When an element therein is identical to that of an embodiment of FIGS. 1A and 1B, it is denoted by the same reference numeral, and the description thereof is not repeated.

FIGS. 3A and 3B show another embodiment of the invention. In this embodiment, the arrangement is identical to that shown in FIGS. 1A and 1B, apart from the fact that, in this embodiment, the hooks extend over the entire width of the web with hooks, which thus does not comprise a selvedge. In this embodiment, the region with hooks overlaps each of the points or edges of the two elastic films 3 and 4.

In FIG. 3B the cutting lines for forming the tabs with hooks are identical to the cutting lines of FIG. 3A.

FIGS. 4A and 4B show yet another embodiment of the invention. In this embodiment, the only difference with respect to the embodiment of FIGS. 1A and 1B is that the hooks are distributed according to zones in the form of discontinuous islands, and not, as in the case of FIGS. 1A and 1B, according to a continuous strip in the direction MD.

Thus, in the direction MD, the central region of hooks is formed by a row, extending in the direction MD, of discontinuous islands separated from one another by separation regions without hooks.

Furthermore, the cutting lines of the tabs shown in FIG. 4B are identical to those of FIG. 1B. However, the inclined lines 19g, 19d and 20g, 20d extend merely in the separation regions and the selvedge zones, and never pass through an island with hooks, such that an island is located, each time, in the centre of a respective tongue-shaped part 13g, 13d.

FIGS. 5A and 5B show another embodiment of the invention. The elastic laminate with hooks, in cross-section according to the direction CD, extends perpendicularly to FIG. 5A over a very significant length (the laminate is intended to be unwound), and over a given width L of the laminate. The elastic laminate with hooks comprises an elastic laminate which comprises a lower layer 1 of nonwoven fabric, an upper layer 2 of nonwoven fabric and, interposed between the two upper and lower layers of nonwoven fabric, an elastic film 3 which is arranged centrally and has a width Le that is smaller than the width L of the laminate. The rigidity of each layer 1 and 2 of nonwoven fabric is constant over its entire width in the direction CD. The laminate also comprises a web 5 with hooks which is arranged so as to be offset with respect to the centre (in the case shown, towards the left) and is formed by a base strip 6 from which hooks 7 protrude.

A nonwoven fabric element with hooks is thus formed by the assembly formed by the lower layer 1 of nonwoven fabric, the upper layer 2 of nonwoven fabric, and the web 5 with hooks, as well as optional layers of adhesive or glue between the two layers of nonwoven fabric, between the upper layer of nonwoven fabric and the web with hooks, and between the layers of nonwoven fabric and the elastic film.

The elastic film 3 is attached, respectively on the top and on the bottom, to the two layers 1 and 2 of nonwoven fabric, for example by means of glue, in particular strips of glue which are not necessarily continuous and may in particular be implemented in the form of glue dots or glue lines. Furthermore, it is also possible to provide glue and/or optionally additional reinforcing elements (not shown in the figures) between the two lower and upper nonwoven fabrics 1 and 2, outside the elastic film.

The elastic film 3 extends between two left-hand and right-hand end edges which, in the figure, in the cross-section CD, form two end points Pg3 and Pd3, left-hand and right-hand respectively, of the elastic film 3.

The base strip 6 of the web 5 with hooks extends between two left-hand and right-hand end edges which, in the figure, in the cross-section CD, form two end points Pg6 and Pd6, left-hand and right-hand respectively, of the base strip.

The base strip 6 comprises two selvedge regions, left-hand and right-hand, 7g and 7d, from which no hooks protrude, and a central region 9 from which hooks 10 protrude. The central region 9 with hooks is delimited by two left-hand and right-hand end edges which, in the figure, in the cross-section CD, form two end points Pg10 and Pd10, left-hand and right-hand respectively, of the central region 9.

The web 5 with hooks is attached by means of gluing, thermal lamination, ultrasonic welding, or the like, of the lower face of the base strip 6 to the upper face of the upper layer 2 of nonwoven fabric.

For the nonwoven fabric element 8 with hooks, it is possible to define a zone of first rigidity, which corresponds to the rigidity of the two layers 1 and 2 of nonwoven fabric taken individually together with the adhesive therebetween, i.e. in the two regions to the left-hand and right-hand side of the web 5 with hooks, which extend on the one hand from the left-hand end edge of the two layers 1 and 2 of nonwoven fabric as far as the left-hand edge Pg6 of the base strip 6, and on the other hand from the right-hand edge Pd6 of the base strip 6 as far as the right-hand end edge of the two nonwoven fabric layers 1 and 2.

It is also possible to define a zone of greater rigidities which extends between the end edges Pg6 and Pd6 and which simultaneously includes the part of the layers 1 and 2 of nonwoven fabric located below these two edges and the web 5 with hooks. In the region of the central region 9 with hooks, the rigidity of the zone of greater rigidities is greater, compared with the first rigidity, than the rigidity in the region of the selvedges 7g and 7d without hooks. Nevertheless, in these two zones of different rigidities, each rigidity is, however, greater than the first rigidity, which corresponds to the lowest rigidity that can be defined for a zone of the nonwoven fabric element 8.

Viewed in cross-section CD, the web 5 with hooks is located on top of the elastic laminate and above the elastic film 3, and the end edge or point Pg6 of the web with hooks of the nonwoven fabric element 8 with hooks is located vertically in line with the elastic film 3, while the end edge or point Pd6 of the web with hooks is not vertically in line with the elastic film 3 (or overhangs said film), and in particular is vertically in line with a point that is at a distance, in the transverse direction, from the elastic film 3, in the direction moving away from the elastic film. Thus, the web with hooks of the nonwoven fabric element overlaps the right-hand end point Pd3 of the elastic film 3.

Viewed in cross-section CD, the end edge or point Pg6 of the zone of greater rigidities of the nonwoven fabric element 8 with hooks is located vertically in line with the elastic film 3, while the end edge or point Pd6 of the zone with greatest rigidity is not vertically in line with the elastic film 3 (or overhangs this), and in particular is vertically in line with a point that is at a distance, in the transverse direction, from the elastic film 3, in the direction moving away from the elastic film. Thus, the zone of greater rigidities of the nonwoven fabric element overlaps the right-hand end point Pd3 of the elastic film 3.

In contrast, in this embodiment shown, the central region 9 with hooks does not overlap any point or edge of the two elastic films 3 and 4, remaining entirely in line with the zone extending outside the elastic film 3.

FIGS. 6A and 6B show another embodiment of the invention. In this embodiment, the arrangement is identical to that shown in FIGS. 5A and 5B, apart from the fact that, in this embodiment, the web with hooks comprises just one selvedge zone on the side opposite the elastic film 3, the region with hooks extending from the single selvedge zone of the opposite side as far as the edge of the web with hooks on the side of the elastic film 3. It follows that, in this embodiment, the region with hooks also overlaps the edge of the elastic film 3 which is overlapped by the web with hooks.

FIGS. 7A and 7B show another embodiment of the invention. In this embodiment, the arrangement is identical to that shown in FIGS. 5A and 5B, apart from the fact that, in this embodiment, the hooks extend over the entire width of the web with hooks, which thus does not comprise a selvedge. It follows that, in this embodiment, the region with hooks, just like the web with hooks, overlaps the edge of the elastic film 3.

FIGS. 8A and 8B show yet another embodiment of the invention. In this embodiment, the only difference with respect to the embodiment of FIGS. 5A and 5B is that the hooks are distributed according to zones in the form of discontinuous islands, and not, as in the case of FIGS. 5A and 5B, according to a continuous strip in the direction MD. Thus, in the direction MD, the central region of hooks is formed by a row, extending in the direction MD, of discontinuous islands separated from one another by separation regions without hooks.

FIGS. 9A and 9B show another embodiment of the invention. The elastic laminate, shown there in cross-section according to the direction CD, extends perpendicularly to FIG. 9A over a very significant length (the laminate is intended to be unwound), and over a given width L of the laminate. The elastic laminate with hooks comprises an elastic laminate which comprises a lower layer 1 of nonwoven fabric, an upper layer 2 of nonwoven fabric and, interposed between the two upper and lower layers of nonwoven fabric, a central elastic film 3 which has a width Le that is smaller than the width L of the laminate. The rigidity of each layer 1 and 2 of nonwoven fabric is constant over its entire width in the direction CD. The elastic laminate with hooks also comprises two left-hand and right-hand webs 5g, 5d with hooks which are each formed of a base strip 6g, 6d, left-hand and right-hand respectively, from each of which hooks 10 protrude. A nonwoven fabric element with hooks is thus formed by the assembly formed of the upper layer 2 of nonwoven fabric and the webs 5g, 5d with hooks. The elastic film 3 is attached, respectively on the top and on the bottom, to the two layers 1 and 2 of nonwoven fabric, for example by means of glue, in particular strips of glue which are not necessarily continuous and may in particular be implemented in the form of glue dots or glue lines. Furthermore, it is also possible to provide glue and/or optionally additional reinforcing elements (not shown in the figures) between the two lower and upper nonwoven fabrics 1 and 2, outside the elastic film.

The elastic film 3 extends between two left-hand and right-hand end edges which, in the figure, in the cross-section CD, form two end points Pg3 and Pd3, left-hand and right-hand respectively, of the elastic film 3.

The base strip 6g of the web 5g with hooks extends between two left-hand and right-hand end edges which, in FIG. 9A, in the cross-section CD, form two end points Pgg6 and Pgd6, left-hand and right-hand respectively, of the base strip 6g.

The base strip 6g comprises two selvedge regions, left-hand and right-hand, from which no hooks protrude, and a central region 9g from which hooks 10 protrude. The central region 9g with hooks is delimited by two left-hand and right-hand end edges which, in the figure, in the cross-section CD, form two end points Pgg10 and Pdg10, left-hand and right-hand respectively, of the central region 9g.

The base strip 6d of the web 5d with hooks extends between two left-hand and right-hand end edges which, in FIG. 9A, in the cross-section CD, form two end points Pdg6 and Pdd6, left-hand and right-hand respectively, of the base strip 6d.

The base strip 6d comprises two selvedge regions, left-hand and right-hand, from which no hooks protrude, and a central region 9d from which hooks 10 protrude. The central region 9d with hooks is delimited by two left-hand and right-hand end edges which, in the figure, in the cross-section CD, form two end points Pgd10 and Pdd10, left-hand and right-hand respectively, of the central region 9d.

The webs 5g, 5d with hooks are each attached by means of gluing, thermal lamination, ultrasonic welding, or the like, of the lower face of the base strip 6g, 6d to the upper face of the upper layer 2 of nonwoven fabric.

For the nonwoven fabric element with hooks (made up of two nonwoven fabric layers 1 and 2, and two webs 5g and 5d with hooks, as well as, optionally, adhesive interposed therebetween), it is possible to define a zone of first rigidity, which corresponds to the rigidity of the two layers 1 and 2 of nonwoven fabric taken individually, i.e. in the two regions to the left-hand side of the web 5g with hooks and to the right-hand side of the web 5d with hooks, and in the region between the two webs 5g and 5d, which extend on the one hand from the left-hand end edge of the two layers 1 and 2 of nonwoven fabric as far as the left-hand edge Pgg6 of the base strip 6g, and on the other hand from the right-hand edge Pdd6 of the base strip 6d as far as the right-hand end edge of the two nonwoven fabric layers 1 and 2, as well as between the two edges Pgd6 and Pdg6 respectively, of the base strips 6g, 6d.

It is also possible to define two zones of greater rigidities, a first zone which extends between the end edges Pgg6 and Pdg6 and which simultaneously includes the part of the two layers 1 and 2 of nonwoven fabric located in line with or below these two edges and the web 5g with hooks, and a second zone which extends between the end edges Pgd6 and Pdd6 and which simultaneously includes the part of the two layers 1 and 2 of nonwoven fabric that are located in line with or below these two edges and the web 5d with hooks. In the region of the central regions 9g and 9d with hooks, the rigidity of the two first and second zones of greater rigidities is greater, compared with the first rigidity, than the rigidity in the region of the selvedges without hooks. Nevertheless, in these two zones of different rigidities, each rigidity is, however, greater than the first rigidity, which corresponds to the lowest rigidity that can be defined for a zone of the nonwoven fabric element.

Viewed in cross-section CD, the web 5d with hooks is located on top of the elastic laminate and above the elastic film 3, and the end edge or point Pdg6 of the web 5d with hooks is located vertically in line with the elastic film 3, while the end edge or point Pgg6 of the web 5d with hooks is not vertically in line with the elastic film 3 (or overhangs said film), and in particular is vertically in line with a point that is at a distance, in the transverse direction, from the elastic film 3. Thus, the web 5*d* with hooks overlaps the left-hand end point Pg3 of the elastic film 3.

Viewed in cross-section CD, the web 5*g* with hooks is located on top of the elastic laminate and above the elastic film 3, and the end edge or point Pgd6 of the web 5*g* with hooks is located vertically in line with the elastic film 3, while the end edge or point Pdd6 of the web 5*g* with hooks is not vertically in line with the elastic film 3 (or overhangs said film), and in particular is vertically in line with a point that is at a distance, in the transverse direction, from the elastic film 3. Thus, the web 5*g* with hooks overlaps the right-hand end point Pd3 of the elastic film 3.

Viewed in cross-section CD, the end edge or point Pdg6 of the first zone of greater rigidities of the nonwoven fabric element is located vertically in line with the elastic film 3, while the end edge or point Pgg6 of the first zone of greater rigidities is not vertically in line with the elastic film 3 (or overhangs said film), and in particular is vertically in line with a point that is at a distance, in the transverse direction, from the elastic film 3. Thus, the first zone of greater rigidities of the nonwoven fabric element overlaps the left-hand end point Pg3 of the elastic film 3.

Viewed in cross-section CD, the end edge or point Pgd6 of the second zone of greater rigidities of the nonwoven fabric element is located vertically in line with the elastic film 3, while the end edge or point Pdd6 of the second zone of greater rigidities is not vertically in line with the elastic film 3 (or overhangs said film), and in particular is vertically in line with a point that is at a distance, in the transverse direction, from the elastic film 3. Thus, the second zone of greater rigidities of the nonwoven fabric element overlaps the right-hand end point Pd3 of the elastic film 3.

In contrast, in this embodiment shown, the central regions 9*g*, 9*d* with hooks do not overlap any point or edge of the elastic film 3, remaining entirely in line with the zone extending outside the elastic film 3.

The laminate of FIGS. 9A and 9B is cut according to a technique said to be full-width. Cutting lines extend on either side of the laminate in order to thus form successive tabs 110*g*, 110*d* or lugs, having a large left-hand side and a large right-hand side respectively.

Each tab 110*g* having a large left-hand side is delimited by an upper cutting line 120*s* which is inclined with respect both to the direction MD and to the direction CD, a lower cutting line 120*i* which is inclined with respect to the direction MD and to the direction CD, the angles of inclination with respect to the direction CD of the two cutting lines 120*s* and 120*i* having the same value but opposing signs, such that each tab 110*g* is further delimited by two lines extending along the left-hand and right-hand edges of the laminate, the line 130*g* extending along the left-hand edge of the tab 110*g* having a large left-hand side extending, given the inclinations of the two cutting lines 120*s* and 120*i*, over a greater distance than the line 130*d* extending along the right-hand edge of the laminate.

Each tab 110*d* having a large right-hand side is delimited by an upper cutting line 140*s* which is inclined with respect both to the direction MD and to the direction CD, a lower cutting line 140*i* which is inclined with respect to the direction MD and to the direction CD, the angles of inclination with respect to the direction CD of the two cutting lines 140*s* and 140*i* having the same value but opposing signs, such that each tab 110*d* is further delimited by two lines extending along the left-hand and right-hand edges of the laminate, the line 150*s* extending along the right-hand edge of the tab 110*d* having a large right-hand side extending, given the inclinations of the two cutting lines 140*s* and 140*i*, over a greater distance than the line 150*g* extending along the right-hand edge of the laminate. Each cutting line 120*s* is also a cutting line 140*i*, and vice versa. Each cutting line 120*i* is also a cutting line 140*s*, and vice versa.

This cutting is specific in order to form laminates that can be attached to the framework of the layer according to the teaching of document WO2015150709_A1_ in the name of the applicant, a zone with hooks being attached to the framework and then deformed, the other zone, on the other side, being used for attachment according to a hook-and-loop fastening system.

FIGS. 10A and 10B show another embodiment of the invention. In this embodiment, the arrangement is identical to that shown in FIGS. 9A and 9B, apart from the fact that, in this embodiment, the two webs with hooks each comprise just one selvedge zone on the side opposite the elastic film 3, the region with hooks of each web with hooks extending from the single selvedge zone of the opposite side as far as the edge of the web with hooks on the side of the elastic film 3. It follows that, in this embodiment, the region with hooks also overlaps the respective edge of the elastic film 3 which is overlapped by the respective web with hooks.

FIGS. 11A and 11B show another embodiment of the invention. In this embodiment, the arrangement is identical to that shown in FIGS. 9A and 9B, apart from the fact that, in this embodiment, the hooks extend over the entire width of each web with hooks, which thus do not comprise a selvedge. It follows that, in this embodiment too, the region with hooks also overlaps the respective edge of the elastic film 3 which is overlapped by the respective web with hooks.

According to an embodiment that is not shown in the figures, it would be possible to provide yet another embodiment of the invention in which the only difference with respect to the embodiment of FIGS. 9A and 9B is that the hooks are distributed according to zones in the form of discontinuous islands, and not, as in the case of FIGS. 9A and 9B, according to a continuous strip in the direction MD. Thus, in the direction MD, the central region of hooks is formed by a row, extending in the direction MD, of discontinuous islands separated from one another by separation regions without hooks.

FIGS. 12A and 12B show another embodiment of the invention. The elastic laminate, shown there in cross-section according to the direction CD, extends perpendicularly to FIG. 12A over a very significant length (the laminate is intended to be unwound), and over a given width L of the laminate. The elastic laminate with hooks comprises an elastic laminate which comprises a lower layer 1 of nonwoven fabric, an upper layer 2 of nonwoven fabric and, interposed between the two upper and lower layers of nonwoven fabric, two elastic films which each have a width Le that is smaller than the width L of the laminate, the sum of the two widths (in this case the two films have the same width Le, but could have different widths) also being less than the width L of the laminate. The rigidity of each layer 1 and 2 of nonwoven fabric is constant over its entire width in the direction CD. The elastic laminate with hooks also comprises four left-hand and right-hand webs 5*g*, 5*d*, 5'*g*, 5'*d* with hooks which are each formed of a base strip 6*g*, 6'*g*, 6*d*, 6'*d*, left-hand and right-hand respectively, from each of which hooks 10 protrude. A nonwoven fabric element with hooks is thus formed by the assembly made up of the upper layer 2 of nonwoven fabric and the webs 5*g*, 5*d*, 5'*g*, 5'*d* with hooks. Each elastic film is attached, respectively on the top and on the bottom, to the two layers 1 and 2 of nonwoven fabric, for example by means of glue, in particular strips of glue which are not necessarily continuous and may in particular be implemented in the form of glue dots or glue lines. Furthermore, it is also possible to provide glue and/or, optionally, additional reinforcing elements (not shown in the figures) between the two lower and upper nonwoven fabrics 1 and 2, outside the elastic films.

Each elastic film extends between two left-hand and right-hand end edges which, in FIG. 12A, in the cross-section CD, form two end points, left-hand and right-hand respectively, of each elastic film.

The base strip 6g of the web 5g with hooks extends between two left-hand and right-hand end edges which, in FIG. 12A, in the cross-section CD, form two end points, left-hand and right-hand respectively, of the base strip 6g.

The base strip 6g comprises two selvedge regions, left-hand and right-hand, from which no hooks protrude, and a central region 9g from which hooks 10 protrude. The central region 9g with hooks is delimited by two left-hand and right-hand end edges which, in the figure, in the cross-section CD, form two end points, left-hand and right-hand respectively, of the central region 9g.

The base strip 6d of the web 5d with hooks extends between two left-hand and right-hand end edges which, in the figure, in the cross-section CD, form two end points Pgd6 and Pdd6, left-hand and right-hand respectively, of the base strip 6d.

The base strip 6d comprises two selvedge regions, left-hand and right-hand, from which no hooks protrude, and a central region 9d from which hooks protrude. The central region 9d with hooks is delimited by two left-hand and right-hand end edges which, in FIG. 12A, in the cross-section CD, form two end points, left-hand and right-hand respectively, of the central region 9d.

The webs 5g, 5d with hooks are each attached by means of gluing, thermal lamination, ultrasonic welding, or the like, of the lower face of the base strip 6g, 6d to the upper face of the upper layer 2 of nonwoven fabric.

The base strip 6'g of the web 5'g with hooks extends between two left-hand and right-hand end edges which, in the figure, in the cross-section CD, form two end points, left-hand and right-hand respectively, of the base strip 6'g.

The base strip 6'g comprises two selvedge regions, left-hand and right-hand, 7'g and 8'g, from which no hooks protrude, and a central region 9'g from which hooks protrude. The central region 9'g with hooks is delimited by two left-hand and right-hand end edges which, in the figure, in the cross-section CD, form two end points, left-hand and right-hand respectively, of the central region 9'g.

The base strip 6'd of the web 5'd with hooks extends between two left-hand and right-hand end edges which, in the figure, in the cross-section CD, form two end points, left-hand and right-hand respectively, of the base strip 6'd.

The base strip 6'd comprises two selvedge regions, left-hand and right-hand, from which no hooks protrude, and a central region 9'd from which hooks protrude. The central region 9'd with hooks is delimited by two left-hand and right-hand end edges which, in the figure, in the cross-section CD, form two end points, left-hand and right-hand respectively, of the central region 9'd.

The webs 5'g, 5'd with hooks are each attached by means of gluing, thermal lamination, ultrasonic welding, or the like, of the lower face of the base strip 6'g, 6'd to the upper face of the upper layer 2 of nonwoven fabric.

For the nonwoven fabric element with hooks (made up of two nonwoven fabric layers 1 and 2, and four webs 5g, 5'g, 5d and 5'd with hooks, as well as, optionally, adhesive layers interposed therebetween), it is possible to define a zone of first rigidity, which corresponds to the rigidity of the two layers 1 and 2 of nonwoven fabric taken individually, i.e. in the two regions to the left-hand side of the web 5g with hooks and to the right-hand side of the web 5'd with hooks, and in the regions between the webs 5g and 5d, between the webs 5d and 5'g, and between the webs 5'g and 5'd.

It is also possible to define four zones of greater rigidities, a first zone which simultaneously includes the web 5g and the part of the layers 1 and 2 of nonwoven fabric located below the web 5g with hooks, and a second zone which simultaneously includes the web 5d and the part of the two layers 1 and 2 of nonwoven fabric located below the web 5d with hooks, a third zone which simultaneously includes the web 5'g and the part of the two layers 1 and 2 of nonwoven fabric located below the web 5'g with hooks, and a fourth zone which simultaneously includes the web 5'd and the part of the two layers 1 and 2 of nonwoven fabric located below the web 5'd with hooks. In the region of the central regions 9g and 9d with hooks, the rigidity of the four first, second, third and fourth zones of greater rigidities is greater, compared with the first rigidity, than the rigidity in the region of the selvedges without hooks. Nevertheless, in these zones of different rigidities, each rigidity is, however, greater than the first rigidity, which corresponds to the lowest rigidity that can be defined for a zone of the nonwoven fabric element.

Viewed in cross-section CD, the web 5g with hooks is located on top of the elastic laminate and above the elastic film 3, and the right-hand end edge or point of the web 5g with hooks, or respectively of the first zone of greater rigidities of the nonwoven fabric element with hooks, is located vertically in line with the elastic film 3, while the other left-hand end edge or point of the web 5g with hooks, or respectively of the first zone of greater rigidities, is not vertically in line with the elastic film 3 (or overhangs said film), and in particular is vertically in line with a point that is at a distance, in the transverse direction, from the elastic film 3. Thus, the web 5g with hooks, or, respectively, the first zone of greater rigidities of the nonwoven fabric element with hooks, overlaps the left-hand end point of the elastic film 3.

Viewed in cross-section CD, the web 5d with hooks is located on top of the elastic laminate and above the elastic film 3, and the left-hand end edge or point of the web 5d with hooks, or respectively of the second zone of greater rigidities of the nonwoven fabric element with hooks, is located vertically in line with the elastic film 3, while the right-hand end edge or point of the web 5d with hooks, or respectively of the second zone of greater rigidities, is not vertically in line with the elastic film 3 (or overhangs said film), and in particular is vertically in line with a point that is at a distance, in the transverse direction, from the elastic film 3. Thus, the web 5d with hooks, or, respectively, the second zone of greater rigidities of the nonwoven fabric element with hooks, overlaps the right-hand end point of the elastic film 3.

Viewed in cross-section CD, the web 5'g with hooks is located on top of the elastic laminate and above the elastic film 4, and the right-hand end edge or point of the web 5'g with hooks, or respectively of the third zone of greater rigidities of the nonwoven fabric element with hooks, is located vertically in line with the elastic film 4, while the other left-hand end edge or point of the web 5'g with hooks, or respectively of the first zone of greater rigidities, is not vertically in line with the elastic film 4 (or overhangs said film), and in particular is vertically in line with a point that is at a distance, in the transverse direction, from the elastic film 4. Thus, the web 5'g with hooks, or, respectively, the third zone of greater rigidities of the nonwoven fabric element with hooks, overlaps the left-hand end point of the elastic film 4.

Viewed in cross-section CD, the web 5'*d* with hooks is located on top of the elastic laminate and above the elastic film 4, and the left-hand end edge or point of the web 5'*d* with hooks, or respectively of the fourth zone of greater rigidities of the nonwoven fabric element with hooks, is located vertically in line with the elastic film 4, while the right-hand end edge or point of the web 5'*d* with hooks, or respectively of the fourth zone of greater rigidities, is not vertically in line with the elastic film 4 (or overhangs said film), and in particular is vertically in line with a point that is at a distance, in the transverse direction, from the elastic film 4. Thus, the web 5'*d* with hooks, or, respectively, the fourth zone of greater rigidities of the nonwoven fabric element with hooks, overlaps the right-hand end point of the elastic film 4.

In contrast, in this embodiment shown, the central regions with hooks do not overlap any point or edge of the elastic films 3 and 4, remaining entirely in line with the zone extending outside the elastic films 3 and 4.

FIGS. 13A and 13B show yet another embodiment of the invention. The elastic laminate, shown there in cross-section according to the direction CD, extends perpendicularly to FIG. 13A over a very significant length (the laminate is intended to be unwound), and over a given width L of the laminate. The elastic laminate with hooks comprises an elastic laminate which comprises a lower layer 1 of nonwoven fabric, an upper layer 2 of nonwoven fabric and, interposed between the two upper and lower layers of nonwoven fabric, an elastic film which has the same width Le as the width L of the laminate. The rigidity of each layer 1 and 2 of nonwoven fabric is constant over its entire width in the direction CD. The elastic laminate with hooks also comprises a web with hooks which is arranged centrally on the upper layer of nonwoven fabric and is formed by a base strip 6 from which hooks 10 protrude.

A nonwoven fabric element with hooks is thus formed by the assembly made up of the upper layer 2 of nonwoven fabric and the web 5 with hooks.

The elastic film is attached, respectively on the top and on the bottom, to the two layers 1 and 2 of nonwoven fabric, for example by means of glue, in particular strips of glue which are not necessarily continuous and may in particular be implemented in the form of glue dots or glue lines.

The base strip 6 of the web 5 with hooks extends between two left-hand and right-hand end edges which, in the cross-section CD, form two end points, left-hand and right-hand respectively, of the base strip. The base strip 6 comprises two left-hand and right-hand selvedge regions 7*g* and 7*d* from which no hooks protrude, and a central region 9 from which hooks 10 protrude. The central region 9 with hooks is delimited by two left-hand and right-hand end edges which, in the cross-section CD, form two end points, left-hand and right-hand respectively, of the central region 9.

The web 5 with hooks is attached by means of gluing, thermal lamination, ultrasonic welding, or the like, of the lower face of the base strip 6 to the upper face of the upper layer 2 of nonwoven fabric.

For the nonwoven fabric element with hooks (made up of the two nonwoven fabric layers 1 and 2, and the web 5 with hooks, as well as optionally the layer of adhesive interposed therebetween), it is possible to define a zone of first rigidity, which corresponds to the rigidity of the two layers 1 and 2 of nonwoven fabric taken individually, i.e. in the two regions to the left-hand and right-hand side of the web 5 with hooks, which extend on the one hand from the left-hand end edge of the two layers 1 and 2 of nonwoven fabric as far as the left-hand edge of the base strip 6, and on the other hand from the right-hand edge of the base strip 6 as far as the right-hand end edge of the two nonwoven fabric layers 1 and 2.

It is also possible to define a zone of greater rigidities which simultaneously includes the part of the two layers 1 and 2 of nonwoven fabric located below the web 5 with hooks and the web 5 itself. In the region of the central region 9 with hooks, the rigidity of the zone of greater rigidities is greater, compared with the first rigidity, than the rigidity in the region of the selvedges 7*g* and 7*d* without hooks. Nevertheless, in these two zones of different rigidities, each rigidity is, however, greater than the first rigidity, which corresponds to the lowest rigidity that can be defined for a zone of the nonwoven fabric element.

Viewed in cross-section CD, the web 5 with hooks is located on top of the elastic laminate and above the elastic film, and the end edge or point of the web 5 with hooks is located vertically in line with the elastic film.

Viewed in cross-section CD, the other end edge or point of the web 5 with hooks is located vertically in line with the elastic film.

Viewed in cross-section CD, the end edge or point of the zone of greater rigidities of the nonwoven fabric element with hooks is located vertically in line with the elastic film.

Viewed in cross-section CD, the other end edge or point of the zone of greater rigidities of the nonwoven fabric element with hooks is located vertically in line with the elastic film.

In this embodiment shown, the central region 9 with hooks also overlaps the elastic film.

FIG. 13B is a plan view of the laminate over some of its length. Dotted lines show cutting lines for cutting the laminate into a succession of tabs with hooks, left-hand and right-hand respectively.

Each tab comprises a substantially rectangular base part and a tongue-shaped part which protrudes laterally from the base part.

Each tab is delimited by cutting lines identical to those defined for the embodiment of FIGS. 1A and 1B.

Thus, the entirety of the central region 9 with hooks is located in the tongue-shaped part 13*g*, 13*d*, and the elastic film extends over the entire base part. However, on account of the overlaps described above, the elastic film extends on the one hand over the entirety of the base part, and on the other hand a part of the elastic film also encroaches into each tongue-shaped part.

FIGS. 14A and 14B show another embodiment of the invention. In this embodiment, the arrangement is identical to that shown in FIGS. 13A and 13B, apart from the fact that, in this embodiment, the hooks extend over the entire width of the web with hooks, which thus does not comprise a selvedge.

FIGS. 15A and 15B show yet another embodiment of the invention. In this embodiment, the only difference with respect to the embodiment of FIGS. 13A and 13B is that the hooks are distributed according to zones in the form of discontinuous islands, and not, as in the case of FIGS. 13A and 13B, according to a continuous strip in the direction MD. Thus, in the direction MD, the central region of hooks is formed in a row, extending in the direction MD, of discontinuous islands separated from one another by separation regions without hooks.

According to another embodiment of the invention that is not shown, it is possible to provide an arrangement that is identical to that shown in FIGS. 13A and 13B, apart from the fact that, in this embodiment, the web with hooks comprises just one selvedge zone, the region with hooks extending from the single selvedge zone of the opposite side as far as the edge of the web with hooks.

FIGS. 16A and 16B describe a laminate that is identical to that of FIGS. 13A and 13B, apart from the fact that the web with hooks is arranged so as to be offset in the direction CD (towards the left in the figures), with respect to the middle of the laminate.

FIGS. 17A and 17B describe a laminate that is identical to that of FIGS. 16A and 16B, apart from the fact that the web with hooks comprises just one single selvedge, on the side of the edge of the laminate closest to the web.

FIGS. 18A and 18B describe a laminate that is identical to that of FIGS. 16A and 16B, apart from the fact that the web with hooks does not comprise a selvedge, the region with hooks extending over the entire width extension of the web with hooks.

FIGS. 19A and 19B describe a laminate that is identical to that of FIGS. 16A and 16B, apart from the fact that the hooks are distributed according to zones in the form of discontinuous islands, and not, as in the case of FIGS. 16A and 16B, according to a continuous strip in the direction MD. Thus, in the direction MD, the central region of hooks is formed by a row, extending in the direction MD, of discontinuous islands separated from one another by separation regions without hooks.

FIGS. 20A and 20B describe a laminate that is identical to that of FIGS. 9A and 9B, apart from the fact that the elastic film extends over the entire width of the laminate.

FIGS. 21A and 21B describe a laminate that is identical to that of FIGS. 20A and 20B, apart from the fact that each web with hooks comprises just one single selvedge, respectively, on the side of the lateral edge of the laminate closest to the respective web, the two selvedges of the two webs thus being opposite one another.

FIGS. 22A and 22B describe a laminate that is identical to that of FIGS. 20A and 20B, apart from the fact that the webs with hooks do not comprise a selvedge, the respective regions with hooks extending over the entire width extension of the respective web with hooks.

FIGS. 23A and 23B describe a laminate that is identical to that of FIGS. 12A and 12B, apart from the fact that the elastic film extends over the entire width of the laminate.

FIG. 24 shows an embodiment that is identical to that of FIGS. 5A and 5B, apart from the fact that the lower layer 1' of nonwoven fabric comprises a reinforced region 30. Thus, the upper layer 2 of nonwoven fabric has a constant rigidity over the entire width CD, while the layer 1' of nonwoven fabric comprises on the one hand two first left-hand and right-hand regions having a first lowest rigidity extending from the left-hand edge, or right-hand, respectively, of the laminate as far as the left-hand edge, or right-hand, respectively, of the reinforced region 30, and on the other hand a second zone which corresponds to the reinforced region and has a greater rigidity. The reinforced region 30, reinforced for example by calendering, in particular hot calendering, extends entirely under the web with hooks, being arranged centrally with respect thereto. The reinforced region 30 does not overlap the edge of the elastic film overlapped by the base strip 6. The edge of the reinforced region on the side of the elastic film is located so as to be substantially at a distance, measured in the direction CD, which is zero from the edge of the elastic film overlapped by the base strip and the web with hooks.

FIG. 25 shows an embodiment that is identical to that of FIGS. 5A and 5B, apart from the fact that the upper layer 2' of nonwoven fabric comprises a reinforced region 31. Thus, the lower layer 1' of nonwoven fabric has a constant rigidity over the entire width CD, while the upper layer 2' of nonwoven fabric comprises on the one hand two first left-hand and right-hand regions having a first lowest rigidity extending from the left-hand edge, or right-hand, respectively, of the laminate as far as the left-hand edge, or right-hand, respectively, of the reinforced region 31, and on the other hand a second zone which corresponds to the reinforced region 31 and has a greater rigidity. The reinforced region 31, reinforced for example by calendering, in particular hot calendering, extends in part under the web 5 with hooks, as well as in part under the central region 9 with hooks. The reinforced region 31 overlaps the edge of the elastic film 3 overlapped by the base strip 6. In this embodiment, the zone of greater rigidities of the nonwoven fabric element with hooks is formed by the reinforced region 31 of the upper layer 2' of nonwoven fabric, the part of the upper layer 2' of nonwoven fabric covered by the web with hooks, the web with hooks, and the part of the lower layer 1' extending under the region 31 and the strip 5, as well as intermediate layers of adhesive or glue.

This zone of greater rigidities, as well as the second zone of greater rigidity of the upper layer of nonwoven fabric, overlaps a side end point of the elastic film 3, while the other side end point of the elastic film is not overlapped by the zone of greater rigidities or the second zone of greater rigidity of the upper layer of nonwoven fabric.

FIG. 26 shows an embodiment that is identical to that of FIG. 25, apart from the fact that the web 5 with hooks on the one hand does not comprise a selvedge, and on the other hand, although being arranged above the elastic film 3, does not overlap the edge of the elastic film 3. In this embodiment, the zone of greater rigidities of the nonwoven fabric element with hooks is formed by the reinforced region 31 of the upper layer 2' of nonwoven fabric, the part of the upper layer 2' of nonwoven fabric covered by the web with hooks, the web with hooks, and the part of the lower layer 1' extending under the region 31 and the strip 5, as well as intermediate layers of adhesive or glue. This zone of greater rigidities, as well as the second zone of greater rigidity of the upper layer of nonwoven fabric, overlaps a side end point of the elastic film 3, while the other side end point of the elastic film is not overlapped either by the zone of greater rigidities of the nonwoven fabric element with hooks, or by the second zone of greater rigidity of the upper layer of nonwoven fabric.

FIG. 27 shows an embodiment that is identical to that of FIG. 24, apart from the fact that the web 5 with hooks on the one hand does not comprise a selvedge, and on the other hand, although being arranged above the elastic film 3, does not overlap the edge of the elastic film 3. In this embodiment, the zone of greater rigidities of the nonwoven fabric element with hooks is formed by the reinforced region 30 of the lower layer 1' of nonwoven fabric, the part of the upper layer 2 of nonwoven fabric covered by the web 5 with hooks, the web with hooks, the rest of the lower layer 1' extending under the strip 5, the rest of the upper layer 2 extending below the reinforced region 30, as well as intermediate layers of adhesive or glue. This zone of greater rigidities, as well as the second zone of greater rigidity of the lower layer of nonwoven fabric, overlaps a side end point of the elastic film 3, while the other side end point of the elastic film is not overlapped either by the zone of greater rigidities of the nonwoven fabric element with hooks, or by the second zone of greater rigidity of the upper layer of nonwoven fabric.

FIG. 28 shows an embodiment of an elastic laminate according to the invention. The elastic laminate with hooks comprises an elastic laminate which comprises two left-hand and right-hand upper layers 201g and 201d of nonwoven fabric, and a lower layer 1' of nonwoven fabric, and two elastic films 3 and 4 which each extend in the direction CD over a width that is smaller than the width of the laminate. The elastic laminate with hooks further comprises a web 5 with hooks. The lower layer 1' of nonwoven fabric extends over the entire width, in the direction CD, of the laminate, having a constant rigidity. The two layers 201g and 201d each extend over a width in the direction CD that is smaller than the total width of the laminate, and the sum of their two widths is smaller than the width of the laminate, such that a gap, referred to as a nonwoven fabric gap, is formed therebetween, on the upper part of the laminate. The two layers of nonwoven fabric each have a respective constant rigidity, and in particular have the same constant rigidity.

The two elastic films 3 and 4 are attached, respectively on the top and on the bottom, to the layers 1' and 201g, respectively 201d, of nonwoven fabric, for example by means of glue, in particular strips of glue which are not necessarily continuous and may in particular be implemented in the form of glue dots or glue lines or by thermal and/or direct (hot) lamination. The elastic film 3 extends between two left-hand and right-hand end edges which, in the figure, form two end points Pg3 and Pd3, left-hand and right-hand respectively, of the elastic film 3. In the same way, the elastic film 4 extends between two left-hand and right-hand end edges which, in the figure, in the cross-section CD, form two end points Pg4 and Pd4, left-hand and right-hand respectively, of the elastic film 4. Thus, a gap referred to as an elastic film gap, which extends between the points Pd3 and Pg4, is defined between the two elastic films.

The base strip 6 of the web 5 with hooks extends between two left-hand and right-hand end edges which, in the figure, in the cross-section CD, form two end points Pg6 and Pd6, left-hand and right-hand respectively, of the base strip, and thus also of the reinforcing element. The base strip 6 comprises two selvedge regions, left-hand and right-hand, from which no hooks protrude (or which are without hooks), and a central region from which hooks protrude. The central region with hooks is delimited by two left-hand and right-hand end edges which, in the figure, in the cross-section CD, form two end points Pg10 and Pd10, left-hand and right-hand respectively, of the central region. The web 5 with hooks is attached by means of gluing, thermal lamination, ultrasonic welding, or the like, of the lower face of the base strip 6 to the upper faces of the upper layers 201g and 201d of nonwoven fabric.

For the nonwoven fabric element 8 with hooks, it is possible to define a zone of first rigidity, which corresponds to the rigidity of the three layers 1', 201d, 201g of nonwoven fabric taken individually together with the adhesive therebetween, i.e. in the two regions to the left-hand and right-hand side of the web 5 with hooks, which extend on the one hand from the left-hand end edge of the layer 201g of nonwoven fabric as far as the left-hand edge Pg6 of the base strip 6, and on the other hand from the right-hand edge Pd6 of the base strip 6 as far as the right-hand end edge of the nonwoven fabric layer 201d. It is also possible to define a zone of greater rigidities which extends between the end edges Pg6 and Pd6 and which simultaneously includes the part of the layers 201g and 201d of nonwoven fabric that are located below the web 5 with hooks. In the region of the central region 9 with hooks, the rigidity of the zone of greater rigidities is greater, compared with the first rigidity, than the rigidity in the region of the selvedges 7g and 7d without hooks. Nevertheless, in these two zones of different rigidities, each rigidity is, however, greater than the first rigidity, which corresponds to the lowest rigidity that can be defined for a zone of the nonwoven fabric element 8.

Viewed in cross-section CD, the end edge or point Pg6 of the reinforcing element in the form of the web 5 with hooks is located vertically in line with the elastic film 3, while the end edge or point Pd6 of the web with hooks is not vertically in line with the elastic film 3 (or overhangs said film), and in particular is vertically in line with a point that is at a distance, in the transverse direction, from the elastic film 3. Thus, the web 5 with hooks overlaps the right-hand end point Pd3 of the elastic film 3.

Viewed in cross-section CD, the end edge or point Pd6 of the web 5 with hooks is located vertically in line with the elastic film 4, while the end edge or point Pg6 of the web 5 with hooks is not vertically in line with the elastic film 4 (or overhangs said film), and in particular is vertically in line with a point that is at a distance, in the transverse direction, from the elastic film 4. Thus, the web 5 with hooks overlaps the left-hand end point Pg4 of the elastic film 4.

Viewed in cross-section CD, the end edge or point Pg6 of the zone of greater rigidities of the nonwoven fabric element 8 with hooks is located vertically in line with the elastic film 3, while the end edge or point Pd6 of the zone of greatest rigidity is not vertically in line with the elastic film 3 (or overhangs said film), and in particular is vertically in line with a point that is at a distance, in the transverse direction, from the elastic film 3. Thus, the zone of greater rigidities of the nonwoven fabric element 8 overlaps the right-hand end point Pd3 of the elastic film 3.

Viewed in cross-section CD, the end edge or point Pd6 of the zone of greater rigidities of the nonwoven fabric element 8 with hooks is located vertically in line with the elastic film 4, while the end edge or point Pg6 of the zone of greatest rigidity is not vertically in line with the elastic film 4 (or overhangs said film), and in particular is vertically in line with a point that is at a distance, in the transverse direction, from the elastic film 4. Thus, the zone of greater rigidities of the nonwoven fabric element 8 overlaps the left-hand end point Pg4 of the elastic film 4. In contrast, in this embodiment shown, the central region 9 with hooks does not overlap any point or edge of the two elastic films 3 and 4, remaining entirely in line with the zone extending between the two left-hand and right-hand elastic films 3 and 4. The web 5 with hooks is attached by two end parts of its lower face to a respective end part of the upper surfaces of two nonwoven fabric layers such that the web 5, and in particular the strip of the web 5, forms a bridge between the two nonwoven fabrics 201g and 201d, on top of the laminate.

The two elastic films are each attached, by the majority of the respective upper face thereof, to the lower face of one of the two layers of nonwoven fabric, the left-hand elastic film 3 being attached to the lower face of the left-hand layer of nonwoven fabric 201g, and the right-hand elastic film 4 being attached to the lower face of the left-hand layer of nonwoven fabric 201g. An inner end part of each elastic 3, 4 protrudes beyond the respective upper layer of nonwoven fabric to which it is attached, in order to be located in the gap between the two layers of nonwoven fabric, directly under the web 5 with hooks.

FIG. 29 shows an embodiment of an elastic laminate with hooks, according to the invention. The elastic laminate with hooks is substantially identical to that of FIG. 28, apart from the fact that the web 5 with hooks, instead of being attached to the two left-hand and right-hand upper layers 201g and

201d of nonwoven fabric on either side of the nonwoven fabric gap, is located on top of the laminate, being directly attached there (except for a layer of glue, adhesive, welding or melt material, or the like) on the two end parts of the elastic films 3 and 4 which protrude into the nonwoven fabric gap, the web with hooks covering the elastic film gap formed between the two elastic films.

Preferably, as shown, the base strip 6 of the web 5 with hooks extends between two left-hand and right-hand end edges (which, in the figure, in the cross-section CD, form two end points Pg6 and Pd6, left-hand and right-hand respectively, of the base strip) over substantially the entirety, or the entirety of the gap between the two upper layers of nonwoven fabric.

For the nonwoven fabric element 8 with hooks, it is possible to define a zone of first rigidity, which corresponds to the rigidity of the three layers 1', 201d, 201g of nonwoven fabric taken individually together with the adhesive therebetween, i.e. in the two regions to the left-hand and right-hand side of the web 5 with hooks, which extend on the one hand from the left-hand end edge of the layer 201g of nonwoven fabric as far as the left-hand edge Pg6 of the base strip 6, and on the other hand from the right-hand edge Pd6 of the base strip 6 as far as the right-hand end edge of the nonwoven fabric layer 201d.

It is also possible to define a zone of greater rigidities which extends between the end edges Pg6 and Pd6 of the web 5 with hooks. In the region of the central region 9 with hooks, the rigidity of the zone of greater rigidities is greater, compared with the first rigidity, than the rigidity in the region of the selvedges without hooks. Nevertheless, in these two zones of different rigidities, each rigidity is, however, greater than the first rigidity, which corresponds to the lowest rigidity that can be defined for a zone of the nonwoven fabric element 8.

Viewed in cross-section CD, the end edge or point Pg6 of the reinforcing element in the form of the web 5 with hooks is located directly (except for the glue or the like) in line with the elastic film 3, while the end edge or point Pd6 of the reinforcing element in the form of the web with hooks is not vertically in line with the elastic film 3 (or overhangs said film), and in particular is vertically in line with a point that is at a distance, in the transverse direction, from the elastic film 3. Thus, the reinforcing element in the form of the web 5 with hooks overlaps the right-hand end point Pd3 of the elastic film 3, being directly (except for the glue or the like) in contact therewith.

Viewed in cross-section CD, the end edge or point Pd6 of the reinforcing element in the form of the web 5 with hooks is located directly (except for the glue or the like) in line with the elastic film 4, while the end edge or point Pd6 of the reinforcing element in the form of the web 5 with hooks is not vertically in line with the elastic film 4 (or overhangs said film), and in particular is vertically in line with a point that is at a distance, in the transverse direction, from the elastic film 4. Thus, the reinforcing element in the form of the web 5 with hooks overlaps the left-hand end point Pg4 of the elastic film 4, being directly (except for the glue or the like) in contact therewith.

Viewed in cross-section CD, the end edge or point Pg6 of the zone of greater rigidities of the nonwoven fabric element 8 with hooks is located vertically in line with the elastic film 3, while the end edge or point Pd6 of the zone of greatest rigidity is not vertically in line with the elastic film 3 (or overhangs said film), and in particular is vertically in line with a point that is at a distance, in the transverse direction, from the elastic film 3. Thus, the zone of greater rigidities of the nonwoven fabric element 8 overlaps the right-hand end point Pd3 of the elastic film 3.

Viewed in cross-section CD, the end edge or point Pd6 of the zone of greater rigidities of the nonwoven fabric element 8 is located vertically in line with the elastic film 4, while the end edge or point Pg6 of the zone of greatest rigidity is not vertically in line with the elastic film 4 (or overhangs said film), and in particular is vertically in line with a point that is at a distance, in the transverse direction, from the elastic film 4. Thus, the zone of greater rigidities of the nonwoven fabric element 8 overlaps the left-hand end point Pg4 of the elastic film 4.

In contrast, in this embodiment shown, the central region 9 with hooks does not overlap any point or edge of the two elastic films 3 and 4, remaining entirely in line with the zone extending between the two left-hand and right-hand elastic films 3 and 4. However, it is possible to provide for the hooks to extend more, in particular over the entire strip 5.

FIG. 30 shows an embodiment that is substantially identical to that of FIG. 27, apart from the fact that, for the lower layer of nonwoven fabric, a reinforcing element in the form of a reinforcing strip 32 which increases rigidity, for example made of a non-elastic thermoplastic material such as polyethylene or polypropylene, is provided in place of the reinforced zone 30, said reinforcing strip being attached to the upper face of the lower layer 1", for example by means of a layer of glue or by welding, in particular ultrasonic welding, thermal welding, or the like. Thus, the upper layer 2 of nonwoven fabric has a constant rigidity over the entire width CD, while the layer 1" of nonwoven fabric comprises on the one hand two first left-hand and right-hand zones having a first lowest rigidity extending from the left-hand edge, or right-hand respectively, of the laminate as far as the left-hand edge, or right-hand respectively, of the reinforcing strip 32, and on the other hand a second zone which corresponds to the reinforcing strip and has a greater rigidity.

In this embodiment, the zone of greater rigidities of the nonwoven fabric element with hooks is formed by the reinforcing strip 32, the region of the lower layer 1" of nonwoven fabric in the region of which the reinforcing strip 32 is attached, the part of the upper layer 2 of nonwoven fabric covered by the web 5 with hooks, the web with hooks, the rest of the lower layer 1" extending below the strip 5, the rest of the upper layer 2 extending above the reinforcing strip 32, as well as intermediate layers of adhesive or glue. This zone of greater rigidities overlaps a side end point of the elastic film 3, while the other side end point of the elastic film is not overlapped by the zone of greater rigidities.

In the cross-section CD shown, the web 5 with hooks extends between two side end points, left-hand Pg5 and right-hand Pd5 respectively, and the reinforcing strip 32 between two side end points, left-hand Pg32 and right-hand Pd32 respectively, such that the reinforcing element extends, in the cross-section CD shown, between the two side end points, left-hand Pg32 and right-hand Pd5 respectively. One (Pg32) of the two side end points (Pg32, Pd5) of the reinforcing element is located vertically in line with a point of the elastic film 3. The other side end point Pd5 of the reinforcing element is not vertically in line with a point of the elastic film (or overhangs the elastic film). Furthermore, one (Pg5) of the two side end points Pg5, Pd5 of the web 5 is located vertically in line with a point of the reinforcing strip 32, while the other point Pd5 is not vertically in line with a point of the reinforcing strip 32. In this embodiment of FIG. 30, the web 5 with hook is located above the elastic film, but no point of the web 5 with hooks is vertically in line with a point of the elastic film.

FIG. 31 shows an embodiment that is identical to that of FIG. 26, apart from the fact that, for the lower layer of nonwoven fabric, a reinforcing element in the form of a reinforcing strip 33 that is identical to the reinforcing strip 32 of FIG. 30, is provided in place of the reinforced zone 30, said reinforcing strip being attached to the lower face of the upper layer 2" of nonwoven fabric, for example by means of a layer of glue or by welding, in particular ultrasonic welding, thermal welding, or the like. Thus, the lower layer 1 of nonwoven fabric has a constant rigidity over the entire width CD, while the upper layer 2" of nonwoven fabric comprises on the one hand two first left-hand and right-hand zones having a first lowest rigidity extending from the left-hand edge, or right-hand respectively, of the laminate as far as the left-hand edge, or right-hand respectively, of the reinforcing strip 33, and on the other hand a second zone which corresponds to the reinforcing strip 33 and has a greater rigidity.

In this embodiment, the zone of greater rigidities of the nonwoven fabric element with hooks is formed by the web 5 with hooks, the reinforcing strip 33, the part of the upper layer 2" of nonwoven fabric reinforced by the reinforcing strip 33 and by the web 5 with hooks, and the part of the lower layer 1 extending under the reinforcing strip 33 and the strip 5, as well as intermediate layers of adhesive or glue. This zone of greater rigidities overlaps a side end point of the elastic film 3, while the other side end point of the elastic film is not overlapped by the zone of greater rigidities.

In the cross-section CD shown, the web 5 with hooks extends between two side end points, left-hand Pg5 and right-hand Pd5 respectively, and the reinforcing strip 33 between two side end points, left-hand Pg33 and right-hand Pd33 respectively, such that the reinforcing element extends, in the cross-section CD shown, between the two side end points, left-hand Pg33 and right-hand Pd5 respectively. One (Pg33) of the two side end points (Pg33, Pd5) of the reinforcing element is located vertically in line with a point of the elastic film 3. The other side end point Pd5 of the reinforcing element is not vertically in line with a point of the elastic film (or overhangs the elastic film).

In this embodiment of FIG. 31, the web 5 with hooks is located above the elastic film, but no point of the web 5 with hooks is vertically in line with a point of the elastic film.

FIG. 32 shows an embodiment that is substantially identical to that of FIG. 26, the only difference being the addition of a reinforcing element in the form of a reinforcing strip 34, identical to the reinforcing strips 32 and 33 of FIGS. 30 and 31, for increasing the rigidity of the lower layer 1''', for example by means of attachment by a layer of glue or by welding, in particular ultrasonic welding, thermal welding, or the like. Thus, the upper layer 2' of nonwoven fabric comprises on the one hand two first left-hand and right-hand zones having a first lowest rigidity extending from the left-hand edge, or right-hand respectively, of the laminate as far as the left-hand edge, or right-hand respectively, of the reinforced region 31, and on the other hand a second zone which corresponds to the reinforced region 31 and which has a greater rigidity, while the lower layer 1''' of nonwoven fabric comprises on the one hand two first left-hand and right-hand zones having a first lowest rigidity extending from the left-hand edge, or right-hand respectively, of the laminate as far as the left-hand edge, or right-hand respectively, of the reinforcing strip 34, and on the other hand a second zone which corresponds to the reinforcing band 34 and which has a greater rigidity.

In this embodiment, the zone of greater rigidities of the nonwoven fabric element with hooks is formed by the web 5 with hooks, the reinforced zone 31 of the upper layer 2', the reinforcing strip 34, the region of the lower layer 1''' of nonwoven fabric in the region of which the reinforcing strip 34 is attached, the part of the upper layer 2' of nonwoven fabric covered by the web 5 with hooks, the rest of the lower layer 1''' extending below the strip 5 and below the reinforced zone 31, the rest of the upper layer 2' extending above the reinforcing strip 34, as well as intermediate layers of adhesive or glue. This zone of greater rigidities overlaps a side end point of the elastic film 3, while the other side end point of the elastic film is not overlapped by the zone of greater rigidities. In this embodiment, two reinforcing elements are provided, i.e. the reinforced zone 31 and the reinforcing strip 34.

In a manner that is common to all the figures, viewed in cross-section CD, of the present application, vertical segments delimiting the overlap zone are shown in all these figures.

In the present application, the rigidity of a zone or region of an element, such as a web, a laminate, a layer of nonwoven fabric, or the like, may for example be measured by means of the process described below.

The rigidity can be measured using a constant elongation rate of a tensile tester under elongation, comprising a computer interface (an appropriate instrument is an MTS Alliance with TestWorks 4 software, available from the company MTS Systems Corp, Eden Prairie, Minnesota), equipped with a 10N charge cell. The tests are performed at 23° C.+−2° C. and at approximately 50% to +−2% relative humidity.

The tester comprises two lateral clamping jaws, for example made of stainless steel, defining therebetween a gap, and a plunge blade, made of a "lightweight" metal such as aluminium, which is arranged centrally, halfway between the jaws, above the gap. The sample is positioned such that two end parts of the region, in which it is desired to study the rigidity of one point in the centre, are each clamped in one of the jaws, such that the point of the sample at which it is desired to measure the rigidity is located exactly below the plunge blade.

Samples measuring 13 mm in width and 25.4 mm in length are cut. If the element does not have sufficient material for samples of this size, the available dimensions are used to compare the rigidity of samples of the same dimensions. The plunge blade is lowered at a constant speed of 500 mm/min over a vertical distance of 25 mm, regulating the acquisition frequency to 200 Hz.

The software is programmed to calculate the maximum peak bending force, and the rigidity (N/m) of the constructed curve giving the force (N) as a function of the elongation (m). The rigidity is calculated as being the gradient of the curve due to bending/elongation for the linear region of the curve, using a minimum line segment of at least 25% of the total peak bending force to calculate the gradient. If the width of the element is not 13 mm, the actual width is standardised to 13 mm, and the corresponding rigidity and peak bending force are calculated by a rule of three.

Some embodiments, which each comprise features distinguishing them from other embodiments, have been described in the figures. Of course, it is also possible to combine these features with one another in order to implement other embodiments of the invention. In particular, features such as the fact of providing just one selvedge or no selvedge, providing two elastic films, providing a web with hooks in the form of islands with hooks, providing an elastic film extending over the entire width, may be combined with other embodiments that do not describe these features in order to thus achieve new embodiments of the invention.

The invention claimed is:

1. An elastic laminate with hooks, having:
   one or more upper layer(s) of nonwoven fabric extending in width in a direction CD and in length in a direction MD;
   one or more elastic film(s) extending in the direction CD over a width, the or each elastic film being attached by an upper face thereof to a lower face of the upper layer or of at least one of the upper layers of nonwoven fabric; and
   one or more web(s) with hooks, the or each web comprising a strip from which hooks protrude and which is attached onto an upper face of the upper layer or of at least one of the upper layer of nonwoven fabric or of the elastic film or of at least one of the elastic films;
   the or each web with hooks extending between respective side end points, left-hand and right-hand respectively, and
   characterised in that
   one of the two side end points, left-hand and right-hand respectively, of the web with hooks or of at least one of the webs with hooks is located vertically in line with a point of an elastic film.

2. The elastic laminate with hooks according to claim 1, characterised in that the or each web comprising a strip from which hooks protrude is attached onto the upper face(s) of the upper layer(s) of nonwoven fabric.

3. The elastic laminate with hooks according to claim 1, characterised in that the elastic film or films extend(s) in the direction CD over a width less than the width in the direction CD of the laminate.

4. The elastic laminate with hooks according to claim 1, characterised in that the other side end point, right-hand and left-hand respectively, of the web with hooks or of the at least one of the webs with hooks is either not vertically in line with a point of an elastic film or extends in a manner overhanging an elastic film.

5. The elastic laminate with hooks according to claim 1, characterised in that it comprises:
   at least two upper layers of nonwoven fabric which extend in width in the direction CD and in length in the direction MD, being spaced apart from one another in the direction CD, defining therebetween a nonwoven fabric gap;
   a web with hooks being attached on either side of the gap, to the upper faces of the two upper layers of nonwoven fabric, covering said nonwoven fabric gap.

6. The elastic laminate according to claim 5, characterised in that it comprises at least two elastic films extending in the direction CD and in length in the direction MD, being spaced apart from one another so as to define therebetween an elastic film gap extending in the nonwoven fabric gap over a width that is less than this gap, each elastic film being attached by an upper face thereof to a lower face of a respective upper layer of nonwoven fabric and the web with hooks being attached to the upper faces of the two upper layers of nonwoven fabric, on either side of the elastic film gap.

7. The elastic laminate with hooks according to claim 1, characterised in that it comprises:
   at least two upper layers of nonwoven fabric extending in width in the direction CD and in length in the direction MD, being spaced apart from one another in the direction CD, defining therebetween a nonwoven fabric gap;
   a web with hooks being attached in the gap, to the upper face of an elastic film.

8. The elastic laminate according to claim 7, characterised in that it comprises at least two elastic films extending in the direction CD and in length in the direction MD, being spaced apart from one another so as to define therebetween an elastic film gap extending in the nonwoven fabric gap over a width that is less than this nonwoven fabric gap, each elastic film being attached by an upper face thereof to the lower face of a respective upper layer of nonwoven fabric and a web with hooks being attached to the upper faces of the two elastic films, on either side of the elastic film gap.

9. The elastic laminate with hooks according to claim 7, characterised in that the web with hooks extends over the entire width or substantially over the entire width of the nonwoven fabric gap.

10. The elastic laminate according to claim 1, characterised in that the strips(s) of the web(s) with hooks is/are laminated to the upper layer(s) of nonwoven fabric such that the strip(s) comprise(s) fibres and/or filaments of the layer(s) of nonwoven fabric.

11. The elastic laminate according to claim 1, characterised in that the or an upper layer of nonwoven fabric comprises a reinforced zone, said reinforcement having been achieved by a local rigidification of the material of the layer of nonwoven fabric, in order to thus form a region inside the upper layer of nonwoven fabric which has a greater rigidity than the rest of the layer of nonwoven fabric.

12. The elastic laminate according to claim 11, characterised in that, at the same time, a web with hooks and the reinforced zone overlap an end edge of an elastic film, each having an end point vertically in line with a point of the elastic film.

13. The elastic laminate according to claim 12, characterized in that the central region of hooks comprises at least one point that is vertically in line with the reinforced zone such that the selvedge region or one of the two selvedge regions, and a part of the central region, are located above the reinforced zone.

14. The elastic laminate according to claim 11, characterised in that the end points opposite the web with hooks and the reinforced zone are not vertically in line with an elastic film.

15. The elastic laminate according to claim 1, characterised in that the or at least one of the webs with hooks comprises a central region (9) from which the hooks protrude, and at least one selvedge region (7g; 7d), from which hooks do not protrude, and the selvedge region or one of the selvedge regions comprises at least one point which is vertically in line with a side edge of an elastic film.

16. The elastic laminate according to claim 15, characterized in that two selvedge regions are provided, and the other selvedge region and the central region are located outside the zone located above the elastic film.

17. The elastic laminate according to claim 1, characterized in that the web with hooks is arranged centrally on the upper face of the laminate.

18. The elastic laminate according to claim 1, characterized in that at least one lower layer of nonwoven fabric is attached to a lower face of the elastic film or films.

19. The elastic laminate according to claim 18, characterized in that the at least one lower layer of nonwoven fabric comprises a reinforced zone arranged under the or one web with hooks.

20. An elastic tab with hooks, intended to be attached to a part of a nappy, the tab comprising an elastic laminate according to claim 1, or being obtained by cutting out from an elastic laminate.

21. A nappy for a baby or adult incontinence pants comprising an upper sheet, a lower sheet, and an absorbent core arranged between the two sheets, and at least one laminate according to claim 1 in order to form the hook tabs originating laterally from the rear waist of the nappy or incontinence pants, such that the hooks engage with loops originating from the front face of the waist of the nappy in order to achieve closure of the nappy or incontinence pants.

22. An assembly forming an elastic laminate with hooks, comprising an elastic laminate and one or more webs with hooks which are arranged on top of the elastic laminate;
- the laminate comprising one or more layers of nonwoven fabric and one or more elastic films attached under at least one layer of nonwoven fabric,
  - the or each layer of nonwoven fabric having either a constant rigidity, or being divided into at least two zones, one first zone in which the layer of nonwoven fabric has a first lowest rigidity, and at least one second zone in which zone or zones of the layer of nonwoven fabric has a rigidity greater than the first rigidity,
  - the web or each of the webs comprising a respective strip from which hooks protrude;
  - the layer or layers of nonwoven fabric possibly comprising one or more reinforcing elements in the form of one or more reinforcing strips, and/or one or more reinforced zones of one or more layers of nonwoven fabric forming one or more second zone(s) of one or more of the layers of nonwoven fabric;

in which:
- the or each web with hooks extends between respective side end points, left-hand and right-hand respectively;
- the or each reinforcing element extends between respective side end points, left-hand and right-hand respectively;

characterised in that
- the web or at least one of the webs (5) with hooks is directly attached, at least in part, to a layer of nonwoven fabric having a constant rigidity, or to said first zone of a layer of nonwoven fabric, or to an elastic film;
- one (Pg6; Pd6) of the two side end points (Pg6, Pd6), left-hand and right-hand respectively, of the web or of at least one of the webs (5) with hooks is located vertically in line with a point of an elastic film; and/or
- one of the two side end points, left-hand and right-hand respectively, of the or at least one of the reinforcing elements is located vertically in line with a point of an elastic film.

\* \* \* \* \*